United States Patent
Toyoda et al.

(10) Patent No.: US 8,262,781 B2
(45) Date of Patent: *Sep. 11, 2012

(54) FUNGI PREVENTING METHOD, FLYING ORGANISM REMOVING APPARATUS AND PLANT PROTECTING APPARATUS BY ADSORPTION OF CONIDIA USING DIELECTRIC POLARIZATION

(75) Inventors: Hideyoshi Toyoda, Kyoto (JP); Yoshinori Matsuda, Kyoto (JP); Teruo Nonomura, Nara (JP); Koji Kakutani, Mie (JP); Shin-ichi Kusakari, Osaka (JP); Katsuhide Higashi, Ibaraki (JP)

(73) Assignees: Kagome Co., Ltd., Aichi (JP); Kinki University, Osaka (JP); Osaka Prefectural Government, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/337,600

(22) Filed: Dec. 27, 2011

(65) Prior Publication Data

US 2012/0090228 A1 Apr. 19, 2012

Related U.S. Application Data

(62) Division of application No. 12/279,186, filed as application No. PCT/JP2007/052562 on Feb. 14, 2007, now Pat. No. 8,105,418.

(30) Foreign Application Priority Data

Feb. 14, 2006 (JP) .................................. 2006-036509

(51) Int. Cl.
*B03C 3/60* (2006.01)
(52) U.S. Cl. ..... 96/66; 47/17; 47/29.3; 47/31; 55/385.2; 95/78; 96/69; 96/96; 96/99
(58) Field of Classification Search .................. 96/66, 69, 96/95–99; 95/78; 55/385.2; 47/17, 29.3, 47/31
See application file for complete search history.

(56) References Cited

U.S. PATENT DOCUMENTS 4,730,633 A * 3/1988 Greenbaum .................... 135/93
5,010,777 A * 4/1991 Yehl et al. .................. 73/864.81
(Continued)

FOREIGN PATENT DOCUMENTS

JP 52-120473 * 10/1977
(Continued)

OTHER PUBLICATIONS

PCT/JP2007/052562, Written Opinion on Form PCT/ISA/237 in Japanese, 4 pages, Apr. 10, 2007.*
(Continued)

*Primary Examiner* — Richard L Chiesa
(74) *Attorney, Agent, or Firm* — Westman, Champlin & Kelly, P.A.

(57) ABSTRACT

A method is provided which can efficiently remove conidia and microbe or the like of a phytopathogen from air and does not cause generation of ozone originated from discharge or so, thereby preventing occurrence of a plant disease without damaging a plant. There are also provided a flying organism removing apparatus and a plant protecting apparatus which can adequately capture flyable organisms, such as spores of a phytopathogen and/or small vermin, by applying an electrostatic field to the flyable organisms. An electrostatic field generated by dielectric polarization is applied to flyable organisms.

12 Claims, 12 Drawing Sheets

U.S. PATENT DOCUMENTS

| | | | | |
|---|---|---|---|---|
| 5,330,559 A | * | 7/1994 | Cheney et al. | 95/63 |
| 5,405,434 A | * | 4/1995 | Inculet | 96/54 |
| 5,807,425 A | * | 9/1998 | Gibbs | 96/66 |
| 5,879,435 A | * | 3/1999 | Satyapal et al. | 96/16 |
| 6,149,717 A | * | 11/2000 | Satyapal et al. | 96/16 |
| 6,764,533 B2 | * | 7/2004 | Lobiondo, Jr. | 96/66 |
| 7,004,995 B2 | * | 2/2006 | Schroder et al. | 95/59 |
| 7,261,767 B2 | * | 8/2007 | Choi et al. | 96/69 |
| 8,105,418 B2 | * | 1/2012 | Toyoda et al. | 95/78 |
| 2002/0073613 A1 | * | 6/2002 | Wijbenga | 47/17 |
| 2002/0170435 A1 | * | 11/2002 | Joannou | 96/66 |
| 2004/0139854 A1 | * | 7/2004 | Rittri et al. | 95/70 |
| 2009/0007781 A1 | * | 1/2009 | Toyoda et al. | 95/57 |

FOREIGN PATENT DOCUMENTS

| | | | | |
|---|---|---|---|---|
| JP | 55-072529 | | 12/1981 | |
| JP | 56-169581 | * | 12/1981 | |
| JP | 60-174440 | * | 9/1985 | |
| JP | 06-178951 | * | 6/1994 | 96/95 |
| JP | 06-079195 | * | 3/1995 | |
| JP | 10-137628 | * | 5/1998 | |
| JP | 2000-189835 | * | 7/2000 | |
| JP | 2002-186364 | * | 7/2002 | |
| JP | 2003-211024 | * | 7/2003 | |
| JP | 2005-204514 | * | 8/2005 | |

OTHER PUBLICATIONS

International Search Report for PCT/JP2007/052562 on Forms PCT/ISA/210 and PCT/ISA/220, 10 pages, Apr. 10, 2007.*

Office Action from related U.S. Appl. No. 12/279,186, mailed Jun. 15, 2011, 6 pages.

* cited by examiner (a)

(b)

(a)

(b)

FUNGI PREVENTING METHOD, FLYING ORGANISM REMOVING APPARATUS AND PLANT PROTECTING APPARATUS BY ADSORPTION OF CONIDIA USING DIELECTRIC POLARIZATION

CROSS-REFERENCE TO RELATED APPLICATION

This application is a Divisional of Ser. No. 12/279,186, filed Aug. 13, 2008, now U.S. Pat. No. 8,105,418 which is a Section 371 National Stage Application of International Application No. PCT/JP2007/052562, filed Feb. 14, 2007, published as WO 2007/094339, not in English, the content of which is hereby incorporated by reference in its entirety.

TECHNICAL FIELD

The present invention relates to a method of preventing occurrence of a plant disease with adsorption removal by charging conidia and microbe or the like, which cause a plant disease, with static electricity.

The present invention also relates to a flying organism removing apparatus and a plant protecting apparatus which prevent occurrence of diseases and insect damages of plants by capturing flyable organisms, such as spores of a phytopathogen and/or small vermin, by applying an electrostatic field to the flyable organisms.

BACKGROUND ART

Natural and chemosynthesis antimicrobial agents and antifungal agents for agriculture are being studied. Some of the antimicrobial agents and antifungal agents for agriculture are put on the market. However, antimicrobial agents and antifungal agents for agriculture, which are in use at present, cannot adequately cope with phytopathogens because of agents having different sensitivities to phytopathogens, phytopathogens becoming resistive to agents, agent-induced sufferings, or the like. In this respect, there is a demand of developing safer and more effective agents in the field of antimicrobial agents and antifungal agents for agriculture.

As natural antimicrobial agents, acetic acid, machine oil, rapeseed oil or the like are put in practical use.

As chemosynthesis antimicrobial agents, benzimidazole antimicrobial agents, such as a thiophanate methyl agent, sterol biosynthesis inhibitors, such as a triadimefon agent and biterthanol agent, anilino pyrimidine microbicide, such as pyrimethanil agent, or the like are put in practical use.

Powdery mildew or the like is caused as conidia fly around in the air, adhere to tomatoes, cucumbers or the like and germinate.

There are air cleaners which remove bacteria, spore, and pollen or the like in the air. The air cleaners which remove bacteria, spore, pollen, or the like, with a filter and/or with electrostatic precipitation are known.

The filter type is not effective unless it has smaller apertures than what is removed, and is difficult to run over a long period of time due to clogging.

An electrostatic induction dust collecting apparatus using two metal electrodes and a plastic three-dimensional mesh screen placed in parallel thereto has been reported as one which increases the effect of capturing dust or mist floating in the air (for example, see Patent Document 1).

An electric dust collecting apparatus of a wire discharge type which applies a high voltage to a metal wire, and an electric dust collecting apparatus of a needle discharge type which applies a high voltage to the tip of a needle are further known (for example, see Patent Document 2, Patent Document 3, and Patent Document 4, or the like). Both of them remove bacteria, spore, pollen, or the like by charging the spore, pollen, or the like to be removed with corona discharge, and making it adsorbed by a collecting electrode.

Diseases and insect damages of vegetables or ornamental flowers if occurred in a greenhouse are very likely to occur on all the plants in the greenhouse. This risk is therefore avoided by pesticide spray before occurrence of diseases and insect damages. It is however difficult, at present, to suppress occurrence of diseases and insect damages of plants without depending on such pesticide spray.

The electrostatic induction dust collecting apparatus which uses metal electrodes and a plastic three-dimensional mesh screen placed in parallel thereto may have corona discharge at the exposed metal electrodes.

While the electric dust collecting apparatus charges spore, pollen, or the like using corona discharge or so, it produces ozone. Accordingly, ozone is likely to adversely affect the plants. Further, the charging efficiency may drop under the condition of a high humidity.

[Patent Document 1] JP-A-52-120473
[Patent Document 2] JP-A-10-137628
[Patent Document 3] JP-A-2000-189835
[Patent Document 4] JP-A-2003-211024

DISCLOSURE OF THE INVENTION

Problems to be Solved by the Invention

The present invention is directed to provide a method of preventing occurrence of a plant disease with adsorption removal by charging conidia and microbe or the like, which cause a plant disease, with static electricity.

The present invention also relates to a flying organism removing apparatus and a plant protecting apparatus which capture flyable organisms, such as spores of a phytopathogen and/or small vermin, by applying an electrostatic field to the flyable organisms.

Means for Solving the Problems

The present inventors made efforts and studied to overcome the problems, then discovered the following solutions and completed the present invention.

According to a method of preventing occurrence of a plant disease according to the present invention, conidia or microbe of a phytopathogen floating in air is charged with a high electrostatic voltage by a non-conductor contacting an electric conductor charged with a high voltage or a non-conductor adjacent thereto, and the charged conidia or microbe is adsorbed by the non-conductor to be removed from the air.

Effects of the Invention

The adsorption removal method which charges conidia and microbe or the like with static electricity according to the present invention can efficiently remove conidia and microbe or the like of a phytopathogen from air and does not cause generation of ozone originated from discharge or so, thereby preventing occurrence of a plant disease without damaging a plant.

It is also possible to adequately capture flyable organisms, such as spores of a phytopathogen and/or small vermin, by applying an electrostatic field to the flyable organisms.

Figure 1:
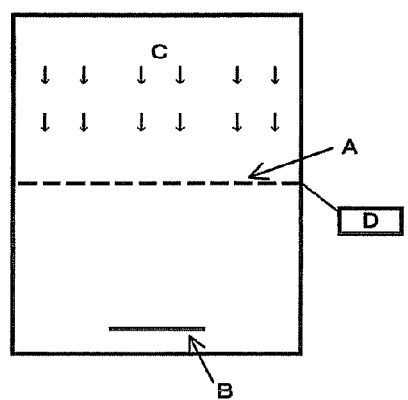
FIG. 1 A conceptual diagram of an apparatus which checks if conidia pass through the grid having electric conductors charged with a high voltage covered with a non-conductor.

FIG. 2 A conceptual diagram (seen from top) of a grid non-conductor portion (dielectric polarization applying section) which is partially in contact with or is adjacent to an electric conductor charged with a high voltage.

FIG. 3 A cross-sectional conceptual diagram of 1, 2 and 3 of the grid non-conductor portion (dielectric polarization applying section) shown in FIG. 2.

FIG. 4 A lateral conceptual diagram as seen from directions 1 to 3 of the grid non-conductor portion (dielectric polarization applying section) shown in FIG. 2.

FIG. 5 A perspective view showing the outline of a plant protecting apparatus 15 according to the present invention.

FIG. 6 A perspective view showing the outline of a flying organism removing apparatus 100.

FIG. 7 A cross-sectional view showing the outline of a flying organism removing apparatus 100.

FIG. 8 A perspective view showing the structure of one dielectric covered conductor 140.

FIG. 9 A cross-sectional view (a) showing the structure of one dielectric covered conductor 140, and a cross-sectional view (b) showing the structure of one dielectric covered conductor 140'.

FIGS. 10 *a-c* Perspective views showing the outlines of dielectric covers 222, 322 and 422.

FIG. 11 A cross-sectional view showing the outline of a flying organism removing apparatus 200.

FIG. 12 A cross-sectional view showing the outline of a flying organism removing apparatus 300.

FIG. 13 A cross-sectional view (a) showing the structure of one dielectric covered conductor 540, and a cross-sectional view (b) showing the structure of one dielectric covered conductor 640.

FIG. 14 A cross-sectional view showing the outline of a flying organism removing apparatus 400.

DESCRIPTION OF REFERENCE NUMERALS

A: dielectric polarization applying section, such as non-conductor covered grid or vertical and horizontal grid
B: slide glass for measuring passed conidia, or location of seedling
C: flow direction of conidia
D: high voltage generating device
1 to 3: numerals indicating positions at the dielectric polarization applying section
10: conductor (e.g., aluminum plate)
11: non-conductor (e.g., polyethylene terephthalate)
12: spacer (which provides a clearance between an electrode portion prepared by a non-conductor and the non-conductor
11)
13: electrode portion (conductor 10 adhered to polyethylene terephthalate and covered with a non-conductor)
14: beam made of polyethylene terephthalate
15: plant protecting apparatus
20: plant arrangement zone
30: surrounding part
32*a*: front wall
32*b*: rear wall
32*c*: right side wall
32*d*: left side wall
32*e*: top surface
32*f*: bottom surface
34*a*, 34*b*: opening
100, 200, 300, 400: flying organism removing apparatus
110, 110*a*, 110*b*: conductor
112, 112*a*, 112*b*: electric conductor
120, 120*a*, 120*b*, 520, 520*a*, 520*b*: dielectric
122, 122', 122*a*, 122*b*, 222, 322, 422: dielectric cover
522, 522*a*, 522*b*, 622: dielectric cover
140, 140', 140*a*, 140*b*: dielectric covered conductor
540, 540*a*, 540*b*, 640: dielectric covered conductor
130: power supply
150: casing

PREFERRED EMBODIMENT FOR CARRYING OUT THE INVENTION

General Description

The method according to the present invention is that to prevent occurrence of the above-mentioned plant disease by using a conductor charged with a high voltage, which is covered with a non-conductor.

Further, the method according to the present invention is that to prevent occurrence of the above-mentioned plant disease by using a non-conductor contacting a conductor charged with a high voltage, which is covered with a non-conductor, or a non-conductor adjacent to the conductor.

A flying organism removing apparatus according to the present invention comprises:

at least one conductor;

a power supply which is electrically connected to the at least one conductor and sets the at least one conductor to a predetermined potential in such a way that an electric field is generated by the at least one conductor; and at least one dielectric located at a position where dielectric polarization is caused by the electric field generated by the at least one conductor, wherein a flyable organism can be captured by an electric field generated via the at least one dielectric.

The flying organism removing apparatus according to the present invention comprises at least one conductor, a power supply and at least one dielectric.

The number of the conductors may be one or plural.

The power supply is electrically connected to at least one conductor. Accordingly, an electric field is generated by the at least one conductor, and the potential of the at least one conductor is set to a predetermined value.

The number of the dielectrics may be one or plural. At least one dielectric is located at a position where dielectric polarization is caused by the electric field generated by the at least one conductor. This dielectric polarization generates an electric field via the at least one dielectric, so that flyable organisms are captured by the electric field.

It is preferable that a dielectric be arranged or formed to have such a shape that the intensity of the electric field generated by dielectric polarization of the dielectric differs according to the position. As an electric field (non-uniform electric field, uneven field) whose field intensity differs according to the position is generated, the Coulomb force can be exerted on the flyable organisms when flyable organisms are charged, and electric induction can be produced at the flyable organism when the flyable organisms are electrically neutral, so that gradient force can be exerted on the flyable organisms. The generation of such an electric field allows the Coulomb force or the gradient force to be exerted on flyable organisms, thus making it difficult for the flyable organisms to move. This can allow the flyable organisms to be adequately captured by an electric field generated by the dielectric polarization of the dielectric.
Figure 2:
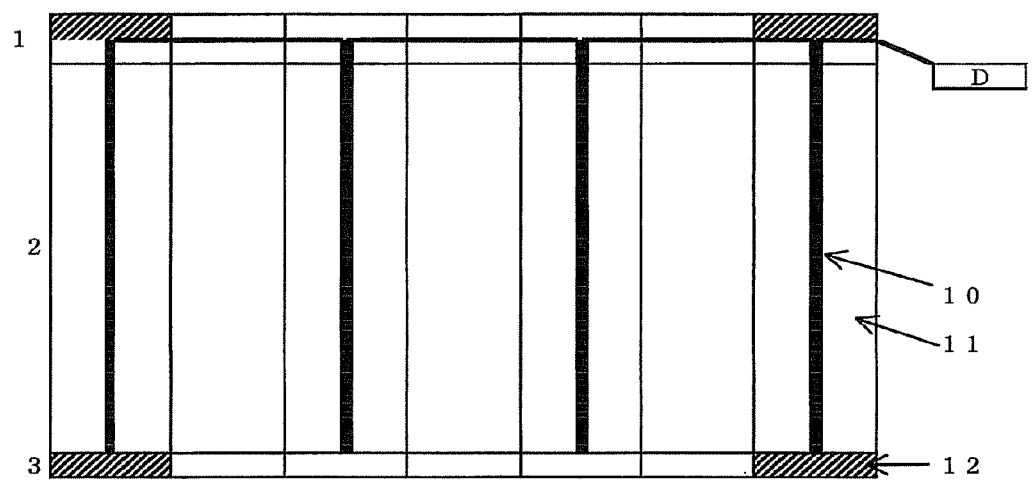

As mentioned above, the number of dielectrics may be at least one. When a plurality of dielectrics are provided, the arrangement of the at least one conductor and the at least one dielectric has only to be combined or modified according to the type of flyable organisms to be removed, the type of plants to be protected by the flying organism removing apparatus, and so forth.

It is preferable that in the flying organism removing apparatus according to the present invention, at least a part of the at least one conductor should be covered with the at least one dielectric.

At least one conductor is covered with a dielectric. The conductor needs to be covered with a dielectric at least partially. Modes of covering at least one conductor with a dielectric include, for example, a mode of covering each of conductors with a dielectric formed into an approximately cylindrical shape, and a mode of covering each of conductors with a dielectric formed into an approximately semicylindrical shape. The shape of the dielectric is not limited to such a shape, and may include a mode of covering the conductor with a dielectric formed by applying or adhering a dielectric material to the conductor.

Further, the flying organism removing apparatus according to the present invention is preferable such that the at least one conductor has a plurality of electric conductors, the at least one dielectric has a plurality of dielectric covers each covering at least a part of a respective one of the plurality of electric conductors, and the plurality of electric conductors covered at least partially by the dielectric covers are arranged to be separated from one another to permit air to flow.

At least one conductor has a plurality of electric conductors. At least one dielectric has a plurality of dielectric covers. Each of the dielectric covers at least a part of a respective one of the plurality of electric conductors.

This eliminates the need to arrange the conductor and dielectric alone, and can allow the dielectric and conductor to be handled together, thus facilitating assembly and handing of the flying organism removing apparatus.

A plurality of electric conductors and a plurality of dielectric covers form plural pairs and those pairs which are adjacent to each other are arranged to be separated from each other so as to permit flow of air. This separate arrangement can permit sufficient air to be supplied to plants to which the air should be supplied via the flying organism removing apparatus. For example, the interval between adjoining pairs has only to be set according to the type of plants to which air should be supplied.

Furthermore, it is preferable that the flying organism removing apparatus according to the present invention should be configured in such a way that each of the plurality of electric conductors has an approximately rod-like shape, each of the plurality of dielectric covers has an approximately cylindrical shape, a plurality of dielectric covered conductors are formed by the plurality of electric conductors and the plurality of dielectric covers, each of the plurality of dielectric covered conductors is formed by a pair of one of the plurality of electric conductors and one of the plurality of dielectric covers, and the one electric conductor is arranged inside the one dielectric cover and along a longitudinal direction thereof, and the plurality of dielectric covered conductors are arranged to be separated from and in parallel to one another to permit air to flow.

Each of the plurality of electric conductors has an approximately rod-like shape. The approximately rod-like shape is an elongated shape extending approximately linearly.

Each of the plurality of dielectric covers has an approximately cylindrical shape. The approximately cylindrical shape is an approximately columnar shape with a through hole formed therein, which extends almost along the longitudinal direction of the approximately columnar shape and penetrating both ends thereof. The through hole need not be concentric, and may be formed eccentric. The through hole has only to be formed inside nearly along the longitudinal direction, and may be formed curved. One example of the approximately cylindrical shape is a cylinder.

A plurality of electric conductors and a plurality of dielectric covers form a plurality of dielectric covered conductors. Specifically, a pair of one of the plurality of electric conductors and one of the plurality of dielectric covers form one dielectric covered conductor, and a plurality of electric conductors and a plurality of dielectric covers form plural pairs, which form a plurality of dielectric covered conductors. In each of the plurality of dielectric covered conductors, the electric conductor is arranged inside the dielectric cover and along the longitudinal direction thereof. That is, the electric conductor is disposed in the through hole formed in the approximately columnar shape. The electric conductor can be disposed in the through hole in the longitudinal direction, and need not be disposed on the axial center line. The electric conductor, if located at a position apart from the axial center line, should be arranged along the longitudinal direction.

This makes it possible to generate an electric field (non-uniform electric field, uneven field) which is generated by the dielectric polarization of each of a plurality of dielectric covers and whose field intensity differs according to the position, exert the Coulomb force or the gradient force on flyable organisms, thus making it difficult for the flyable organisms to move. This can allow the flyable organisms to be adequately captured by an electric field generated by the dielectric polarization of each of a plurality of dielectric covers.

A plurality of dielectric covered conductors are arranged to be separated from and in parallel to one another to permit air to flow. Specifically, adjoining two dielectric covered conductors are arranged to be separated so that air can flow between the two dielectric covered conductors.

This can permit light to be irradiated on plants without blocking the light with a plurality of dielectric covered conductors. Further, it is possible to adequately supply air via the flying organism removing apparatus.

It is preferable that the flying organism removing apparatus according to the present invention should be configured in such a way that each of the plurality of electric conductors has an approximately rod-like shape, each of the plurality of dielectric covers has an approximately semicylindrical shape including an outer surface and an inner surface, a plurality of dielectric covered conductors are formed by the plurality of electric conductors and the plurality of dielectric covers, each of the plurality of dielectric covered conductors is formed by a pair of one of the plurality of electric conductors and one of the plurality of dielectric covers, and the one electric conductor is arranged on an inner surface side of the one dielectric cover and along a longitudinal direction thereof, and the plurality of dielectric covered conductors are arranged to be separated from and in parallel to one another to permit air to flow.

Each of the plurality of electric conductors has an approximately rod-like shape. The approximately rod-like shape is an elongated shape extending approximately linearly.

Each of the plurality of dielectric covers has an approximately semicylindrical shape. The approximately semicylindrical shape is a half of an approximately cylindrical shape which is formed when nearly bisected at a plane including the axial center line. For example, it is a shape formed by nearly bisecting a cylinder at a plane including the axial center line. Each of the dielectric covers, which has an approximately semicylindrical shape, has an outer surface and an inner surface. The outer surface has a small curvature about the axial center, and an approximately semicircular protruding cross section along a plane perpendicular to the axial center line. The inner surface has a larger curvature about the axial center than that of the outer surface, and an approximately semicircular recessed cross section along a plane perpendicular to the axial center line.

A plurality of electric conductors and a plurality of dielectric covers form a plurality of dielectric covered conductors. Specifically, a pair of one of the plurality of electric conductors and one of the plurality of dielectric covers form one dielectric covered conductor, and a plurality of electric conductors and a plurality of dielectric covers form plural pairs, which form a plurality of dielectric covered conductors. In each of the plurality of dielectric covered conductors, the electric conductor is arranged inside the dielectric cover and along the longitudinal direction thereof. The electric conductor can be disposed on the inner surface side of the dielectric cover, and need not be disposed on the axial center line. The electric conductor, if located at a position apart from the axial center line, should be arranged along the longitudinal direction.

This makes it possible to generate an electric field (non-uniform electric field, uneven field) which is generated by the dielectric polarization of each of a plurality of dielectric covers and whose field intensity differs according to the position, exert the Coulomb force or the gradient force on flyable organisms, thus making it difficult for the flyable organisms to move. This can allow the flyable organisms to be adequately captured by an electric field generated by the dielectric polarization of each of a plurality of dielectric covers.

A plurality of dielectric covered conductors are arranged to be separated from and in parallel to one another to permit air to flow. Specifically, adjoining two dielectric covered conductors are arranged to be separated so that air can flow between the two dielectric covered conductors.

This can permit light to be irradiated on plants without blocking the light with a plurality of dielectric covered conductors. Further, it is possible to adequately supply air via the flying organism removing apparatus.

Further, the flying organism removing apparatus according to the present invention is preferably configured in such a way that a plurality of dielectric covered conductor groups are formed by the plurality of dielectric covered conductors, each of the plurality of dielectric covered conductor groups is formed by a predetermined number of dielectric covered conductors in the plurality of dielectric covered conductors, the predetermined number of dielectric covered conductors in the plurality of dielectric covered conductor groups are arranged to be separated from and in parallel to one another to permit air to flow, and each of the plurality of dielectric covered conductor groups is arranged along one surface corresponding to a plurality of predetermined surfaces different from one another.

A plurality of dielectric covered conductor groups are formed by a plurality of dielectric covered conductors. Further, each of the plurality of dielectric covered conductor groups is formed by a predetermined number of dielectric covered conductors. The predetermined of number of dielectric covered conductors belonging to each of the plurality of dielectric covered conductor groups are arranged to be separated from and in parallel to one another to permit air to flow. Specifically, adjoining two dielectric covered conductors belonging to one dielectric covered conductor group are arranged to be separated so that air can flow between the two dielectric covered conductors.

Each of the plurality of dielectric covered conductor groups is arranged along one corresponding side. Dielectric covered conductors belonging to the respective dielectric covered conductor groups are arranged on different sides. That is, dielectric covered conductors belonging to one dielectric covered conductor group are arranged along one side.

This can widen the range of an electric field generated around the dielectric covers of the dielectric covered conductors, and can thus widen the range where flyable organisms can be captured.

Furthermore, the flying organism removing apparatus according to the present invention is preferable configured in such a way that the plurality of dielectric covered conductor groups include a first dielectric covered conductor group and a second dielectric covered conductor group, the first dielectric covered conductor group and the second dielectric covered conductor group are positioned at an outermost surface of the plurality of predetermined surfaces different from one another, and the outer surface of the dielectric cover which forms the first conductor group and the outer surface of the dielectric cover which forms a second conductor group are arranged to face in opposite directions.

The plurality of dielectric covered conductor groups include the first dielectric covered conductor group and the second dielectric covered conductor group. The first dielectric covered conductor group and the second dielectric covered conductor group are positioned at the outermost surface of the dielectric covered conductor groups. The outer surface of the dielectric cover which forms a first conductor group and the outer surface of the dielectric cover which forms a second conductor group are arranged to face in opposite directions. As mentioned above, the shape of the dielectric cover can be formed in an approximately semicylindrical shape including an outer surface and an inner surface. As mentioned above, the outer surface has an approximately semicircular protruding cross section along a plane perpendicular to the axial center line. Arranging the outer surface of the dielectric cover which forms a first conductor group and the outer surface of the dielectric cover which forms a second conductor group to face in opposite directions means that the protruding surfaces are arranged to face in the opposite directions.

Accordingly, even if the shape of the dielectric covers is set to an approximately semicylindrical shape, the electric conductors are not arranged facing outward, but the dielectric covers are arranged facing outward. Even if the electric conductors contact the dielectric covered conductors when a high voltage is applied to the electric conductors, therefore, the electric conductors are insulated by the dielectric covers, thereby ensuring safety.

It is preferable that in the flying organism removing apparatus according to the present invention, the at least one conductor and the at least one dielectric should be arranged so as to cover a predetermined opening formed to permit air to flow.

At least one conductor and at least one dielectric are arranged so as to cover a predetermined opening formed to permit air to flow. The opening can be formed in whatever the flying organism removing apparatus is provided. The flying organism removing apparatus is provided at, for example, a plant protecting apparatus, such as a greenhouse or vinyl house. The opening may be formed in such a plant protecting apparatus so that air can flow through the opening.

This makes it possible to exert the Coulomb force or the gradient force on flyable organisms, which will enter through the opening along the flow of air, thereby capturing the flyable organisms.

A plant protecting apparatus according to the present invention includes:
  a plant arrangement zone where a plant is arranged; and
  a surrounding part surrounding the plant arrangement zone,
  wherein at least a part of the surrounding part can transmit visible light, and
  the aforementioned flying organism removing apparatus is provided in the portion of the surrounding part where air can flow.

The plant protecting apparatus according to the present invention includes the plant arrangement zone and the surrounding part. A plant is arranged in the plant arrangement zone. It is applicable to any types of plants. The surrounding part surrounds the plant arrangement zone. The surrounding part is made of a member which can transmit visible light. The surrounding part has a portion where air can flow. It is sufficient that the air needed for growth and existence of plants can be made to flow. The flying organism removing apparatus is provided at the portion where the air can flow. This can remove flyable organisms from the air and supply adequate air for growth and existence of plants.

The plant protecting apparatus according to the present invention is preferably configured in such a way that
  at least one airflow opening for supplying air to the plant arranged in the plant arrangement zone is formed in the surrounding part,
  the flying organism removing apparatus is attached in such a way as to cover the at least one airflow opening,
  the first dielectric covered conductor group is arranged at a position farthermost from the airflow opening, and
  the second dielectric covered conductor group is arranged at a position nearest from the airflow opening.

At least one airflow opening is formed in the surrounding part. The airflow opening serves to supply air to the plant arranged in the plant arrangement zone. The flying organism removing apparatus is attached in such a way as to cover the airflow opening. Further, the first dielectric covered conductor group is arranged at a position farthermost from the airflow opening. That is, the dielectric covered conductors belonging to the first dielectric covered conductor group are arranged at a position farthermost from the airflow opening. The second dielectric covered conductor group is arranged at a position nearest from the airflow opening. That is, the dielectric covered conductors belonging to the second dielectric covered conductor group are arranged at a position nearest from the airflow opening.

Accordingly, at first, flyable organisms which are going to enter the plant arrangement zone from the opening can be captured by the dielectric covered conductors belonging to the first dielectric covered conductor group. Even when flyable organisms cannot be captured by the dielectric covered conductors belonging to the first dielectric covered conductor group, the flyable organisms can be captured by the dielectric covered conductors belonging to the second dielectric covered conductor group arranged at the position nearest from the airflow opening. This can increases the chance of capturing flyable organisms which will enter the plant arrangement zone from the opening.

Even if the shape of the dielectric covers is set to an approximately semicylindrical shape, the electric conductors of the dielectric covered conductors belonging to the first dielectric covered conductor group or the second dielectric covered conductor group are not arranged facing outward, but the dielectric covers are arranged facing outward. Even if the electric conductors contact the dielectric covered conductors when a high voltage is applied to the electric conductors, therefore, the electric conductors are insulated by the dielectric covers, thereby ensuring safety.

Moreover, the plant protecting apparatus according to the present invention is preferably configured in such a way that
  a mesh body formed of a dielectric material in which at least one mesh is formed,
  wherein the mesh body has an area approximately same as an area occupied by the predetermined number of dielectric covered conductors forming the first covered conductor group, and
  the mesh body is arranged at a position near the position of the first covered conductor group and far from the first covered conductor group with respect to the airflow opening in such a way as to cover the dielectric covered conductors forming the first covered conductor group.

The plant protecting apparatus according to the present invention includes a mesh body. The mesh body is formed of a dielectric material and has at least one mesh formed. The mesh can be formed by weaving or bending a wire members formed of a dielectric material, or all or some of meshes can be integrally formed of a dielectric material by forming holes in a plate-like member, so that the mesh can be finally seen as a mesh pattern. The size of one mesh may be determined according to the types or so of flyable organisms. Not all meshes should have the same size. While the preferable shape of the meshes are approximately quadrangle, approximately lozenge or the like, other polygonal shapes may be taken.

The mesh body preferably has an area approximately same as an area occupied by the dielectric covered conductors belonging to the first dielectric covered conductor group. Further, the mesh body is preferably arranged at a position near the position of the first covered conductor group and far from the first covered conductor group with respect to the airflow opening. It is also preferable that the mesh body should cover all of the dielectric covered conductors belonging to the first dielectric covered conductor group.

Accordingly, the mesh body also has the function of a cover for the flying organism removing apparatus, so that movement of objects larger than flyable organisms, such as leaves of plants or dust, can be inhibited by the dielectric mesh body and the objects can be removed so as not to contact the electric conductors.

First Embodiment

In a method of preventing occurrence of a plant disease according to the present invention, any means which can charge conidia and microbe or the like (hereinafter conidia or the like) with a high electrostatic voltage can be used in the present invention. For example, conidia or the like should be charged by dielectric polarization in a non-conductor or by electrostatic induction in a conductor.

Any conductor can be used as a conductor which charges a high voltage. Copper, aluminum, stainless, iron or the like can be exemplified as such conductor. In the present invention, it is preferable to use a conductor covered with a non-conductor because it can suppress corona discharge and prevent an electric-shock originated accident.

A non-conductor contacting a conductor charged with a high voltage, or a non-conductor adjacent to the conductor means the use of a non-conductor contacting a conductor charged with a high voltage, or the use of a non-conductor adjacent to a conductor charged with a high voltage. As such non-conductor, anything which is not electrically conductive or which is called an insulator can be used. Vinyl chloride, polyethylene, polypropylene, urethane, polyester, rayon, cellulose, rubber or the like can be exemplified as such non-conductor. A conductor may be covered with a non-conductor. The covering method is not limited as long as a conductor is covered with a non-conductor. For example, a conductor can be adhered or covered with a non-conductor by melting a non-conductor and applying or coating the non-conductor to the conductor. A paint containing a non-conductor may be used, and the paint is preferably an insulative paint.

A non-conductor adjacent to a conductor charged with a high voltage is a state where a non-conductor is in contact with a part of a conductor, a state where a non-conductor is disposed near a conductor, a state where a non-conductor is in contact with a part of a conductor covered with a non-conductor, or a state where a non-conductor is disposed near a conductor covered with a non-conductor. The "near" is a distance at which a non-conductor can be charged by a conductor or a conductor covered with a non-conductor. For example, the distance is 0.1 to 3 cm, preferably, 0.2 to 2 cm, and more preferably 0.5 to 1 cm.

A non-conductor according to the present invention may have any shape as long as it can charge conidia or the like. For example, a non-conductor having covered copper wires laid out in parallel, a non-conductor having covered copper wires laid out in a vertical and horizontal grid pattern, a net of a non-conductor surrounded by a conductor, a net of a non-conductor surrounded by a conductor covered with a non-conductor, conductor covered with a non-conductor laid out in parallel (which may be in contact with or adjacent to a net) to a net of a non-conductor, and a metal mesh covered with a non-conductor are available.

The interval between non-conductors in the present invention, which will change according to a charge voltage, may take any distance as long as conidia or the like can be charged and adhered.

A charge voltage in the present invention, which differs depending on the interval between non-conductors and the amount of wind that passes through the non-conductor portion, may be any voltage as long as conidia or the like can be charged to a high electrostatic voltage. For example, the voltage is preferably 1 to 30 kV, more preferably 3 to 20 kV, and further preferably 5 to 15 kV. If the charge voltage is too high, conidia or the like may not be adsorbed. If the charge voltage is too low, dielectric polarization of conidia or the like may not be effected, which is not preferable.

A preferable polarity at the time of charging can be selected according to the usage, the installing method and location, or the like. In the present invention, when a conductor is charged to a negative high voltage, the positive polarity is the ground (earth), whereas when a conductor is charged to a positive high voltage, the negative polarity is the ground (earth). That is, a portion where conidia or the like are adsorbed is charged with only a single polarity (either negative or positive). Accordingly, it can be expected that corona discharge from the portion where conidia or the like are adsorbed is mostly eliminated, thereby enabling the use under high humidity.

Conidia in the present invention are asexual spores which infect agricultural plants with a disease and lack mobility. It is to be noted that what is produced by separating hyphae at the partition portion and what is generated by propagating from conidia forming cells are included.

Examples of the targets in the method of preventing occurrence of a plant disease according to the present invention may be powdery mildew (tomato, eggplant, green pepper, wheat, cucumber, melon, watermelon, pea, grape, strawberry, rose, or the like), sclerotial disease (tomato, eggplant, cucumber, watermelon, oriental radish, napa, cabbage, or the like), gray mold (tomato, eggplant, green pepper, cucumber, pumpkin, strawberry, pea, bean, onion, green onion, or the like), leaf mold (tomato or the like), and rust (green onion, onion, chinese leek, asparagus, lettuce, or the like).

Microbe in the present invention is what infects agricultural plants with a disease.

Examples of apparatuses to which the method according to the present invention is adapted include one in which a non-conductor contacting or adjacent to a conductor charged with a high voltage is installed in a filter portion, one in which a non-conductor is provided on a conductor charged with a high voltage into a plate-like shape, wires of covered electric conductors charged with a high voltage, or the like.

As the shape of a non-conductor which causes dielectric polarization of the filter portion, a non-conductor having covered copper wires laid out in parallel, a non-conductor having covered copper wires laid out in a grid pattern, a net of a non-conductor surrounded by an electric conductor, a metal mesh covered with a non-conductor, or the like are exemplified. It is preferable to place the filter in front of the non-conductor which causes dielectric polarization from the viewpoint of removing large things. Such a filter portion can be installed in, for example, the intake portion to a house to supply clean air free of conidia or the like therein, or can be placed in a green house to purify the air in the green house.

A plate-like type or a wire type can be placed in a green house for purification of the air therein or the like.

Further, the apparatus according to the first embodiment can remove small vermin as a target. The small vermin is general winged small vermin which grows in greenhouse horticulture, and may be, for example, aphids, Thripidae, Agomyzidae, Lyonetiidae, Aleyrodidae, Plutella xylostella, and so forth. Also, small vermin (mites) parasitic to winged small vermin to be parasitic to crops for agriculture may also be the target.

Second Embodiment

Plant Protecting Apparatus 15

FIG. 5 is a perspective view showing the outline of a plant protecting apparatus 15 according to the present invention.

<Plant Arrangement Zone 20>

The area surrounded by the broken line shown in FIG. 5 is a plant arrangement zone 20. The plant arrangement zone 20 is located in approximately the center part in the plant protecting apparatus 15. The plant arrangement zone 20 should just be an environment suitable for cultivating plants or making them survive. Particularly, the plant arrangement zone 20 should just be an environment which can sufficiently irradiate light and can sufficiently supply air according to the kinds of plants. It is preferred to secure a sufficient area according to the size of plants and make an environment in which the temperature and humidity are adequately adjusted according to the kinds of plants.

<Surrounding Part 30>

The surrounding part 30 surrounds the plant arrangement zone 20. In the example shown in FIG. 5, the surrounding part 30 is a rectangular parallelepiped and has a front wall 32a, a rear wall 32b, a right side wall 32c, a left side wall 32d, a top surface 32e, and a bottom surface 32f. It is preferable that the front wall 32a, rear wall 32b, right side wall 32c, left side wall 32d, and top surface 32e should be formed of a transparent member which can sufficiently transmit light. For example, they should be formed of transparent glass as well as transparent plastic, such as acrylic resin.

Figure 5:
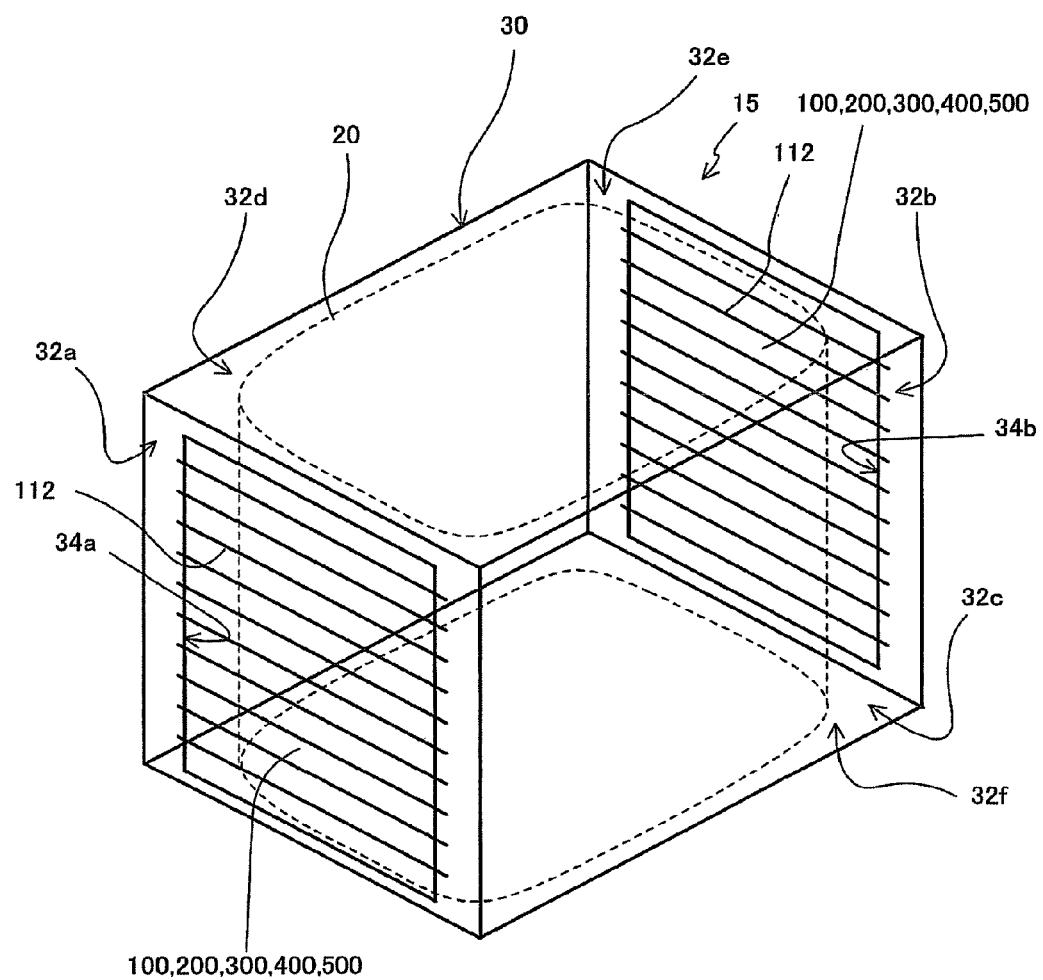

Openings 34a and 34b for supplying air to the plants arranged in the plant arrangement zone 20 are formed in both of the front wall 32a and the rear wall 32b. A flying organism removing apparatuses 100, 200, 300 or 400 to be described later is installed outside each of the openings 34a and 34b so as to cover the openings 34a and 34b. FIG. 5 shows only an electric conductor 112 of the flying organism removing apparatus 100 as one example of the flying organism removing apparatus 100, 200, 300 or 400.

Although the surrounding part 30 is illustrated to be a rectangular parallelepiped as shown in FIG. 5 in the embodiment, it is not limited to such a shape, and it can be anything which can provide an adequate environment to plants placed in the plant arrangement zone 20, and the surrounding part 30 may be formed to have a curved surface.

<Flying Organism Removing Apparatus 100, 200, 300, 400>

As mentioned above, the flying organism removing apparatuses 100, 200, 300 or 400 to be described later is disposed at the opening 34a of the front wall 32a, and the opening 34b of the rear wall 32b.

The flying organism removing apparatuses 100 and 300 include a dielectric covered conductor 140 having an electric conductor 112 and a dielectric cover 122 as described later. The flying organism removing apparatus 200 includes a dielectric covered conductor 140a having an electric conductor 112a and a dielectric cover 122a, and a dielectric covered conductor 140b having an electric conductor 112b and a dielectric cover 122b. The flying organism removing apparatus 400 includes a dielectric covered conductor 540a having an electric conductor 112a and a dielectric cover 522a, and a dielectric covered conductor 540b having an electric conductor 112b and a dielectric cover 522b.

In the above-described plant protecting apparatus 15 shown in FIG. 5, it is illustrated that the openings 34a and 34b are formed in approximately the entire surfaces of the front wall 32a and the rear wall 32b, and the flying organism removing apparatus 100, 200, 300, or 400 is attached so as to cover the two openings 34a and 34b. However there may be a case where it is sufficient to form an opening only in partial areas of the front wall 32a and the rear wall 32b depending on the kinds and number of plants placed in the plant arrangement zone 20. In such a case, the flying organism removing apparatuses 100, 200, and 300 or 400 which has a size according to the size of the formed opening has only to be attached. It is sufficient that the flying organism removing apparatuses 100, 200, and 300 or 400 should supply the suitable air to the plants placed in the plant arrangement zone 20 by covering the entire opening which is formed.

Although FIG. 5 shows a case where the plant protecting apparatus 15 shown therein has the flying organism removing apparatuses 100, 200, 300 or 400 attached only to two places, the front wall 32a and the rear wall 32b, the flying organism removing apparatuses 100, 200, and 300 or 400 may be attached to the other right side wall 32c, the left side wall 32d, the top surface 32e, and so forth. It is sufficient to be able to sufficiently irradiate light plants and sufficiently supply air thereto according to the kinds and number of the plants placed in the plant arrangement zone 20. The quantity and size of the flying organism removing apparatuses 100, 200, and 300 or 400 and the locations for disposing the flying organism removing apparatuses 100, 200, and 300 or 400 may be adequately determined according to the kinds, number, or the like of plants.

As application examples of the plant protecting apparatus 15, the plant protecting apparatus 15 is used as a greenhouse or vinyl house, or is placed and used inside a greenhouse or vinyl house. That is, when the plant protecting apparatus 15 is used as a greenhouse or vinyl house, the flying organism removing apparatuses 100, 200, and 300 or 400 can be attached to the opening portion of the plant protecting apparatus 15. When the plant protecting apparatus 15 is placed and used inside a greenhouse or vinyl house, the flying organism removing apparatuses 100, 200, and 300 or 400 can be attached to a box for growing plants, which is placed inside a greenhouse or vinyl house.

<<Flying Organism Removing Apparatus 100>>

Figure 6:
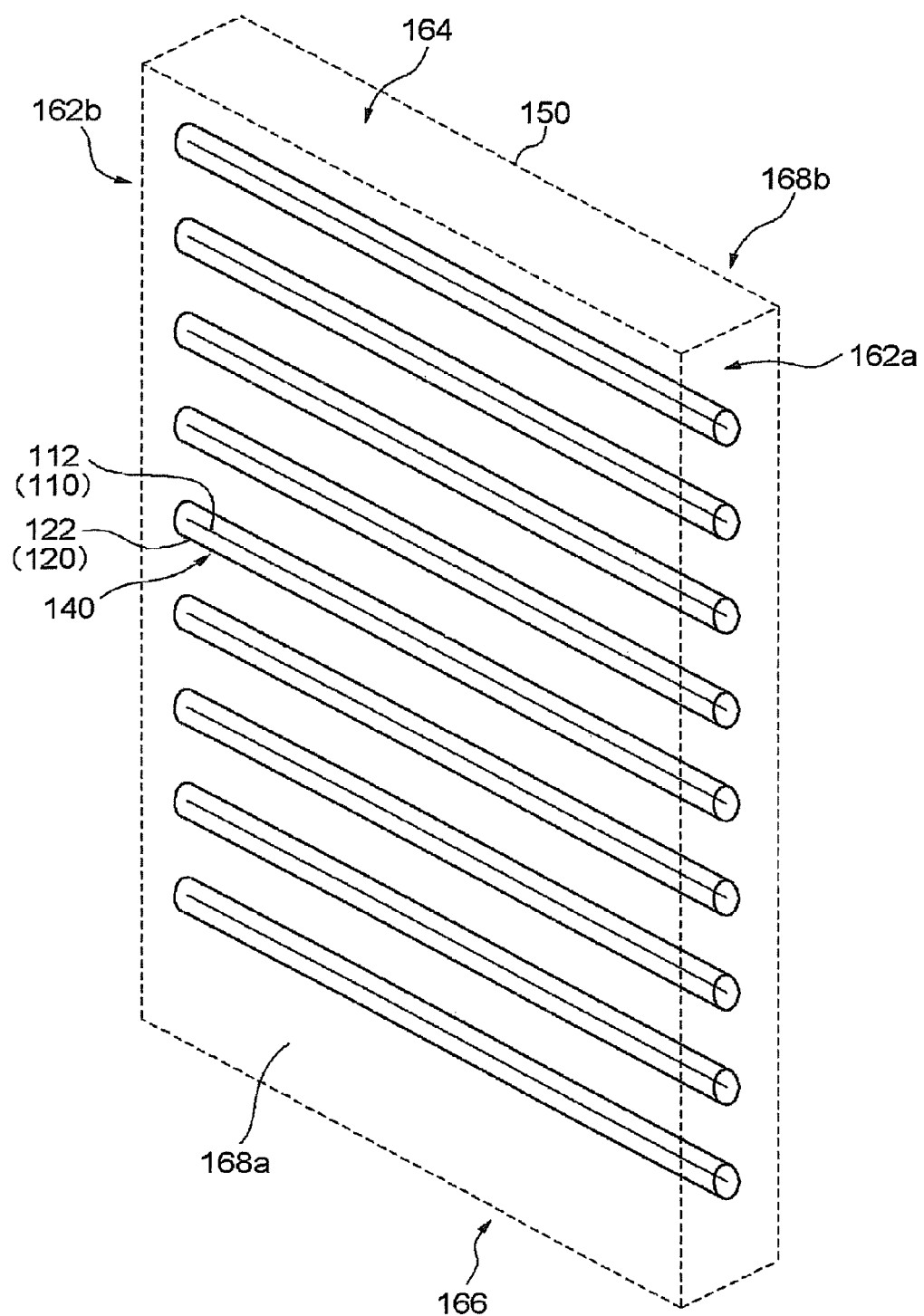
Figure 7:
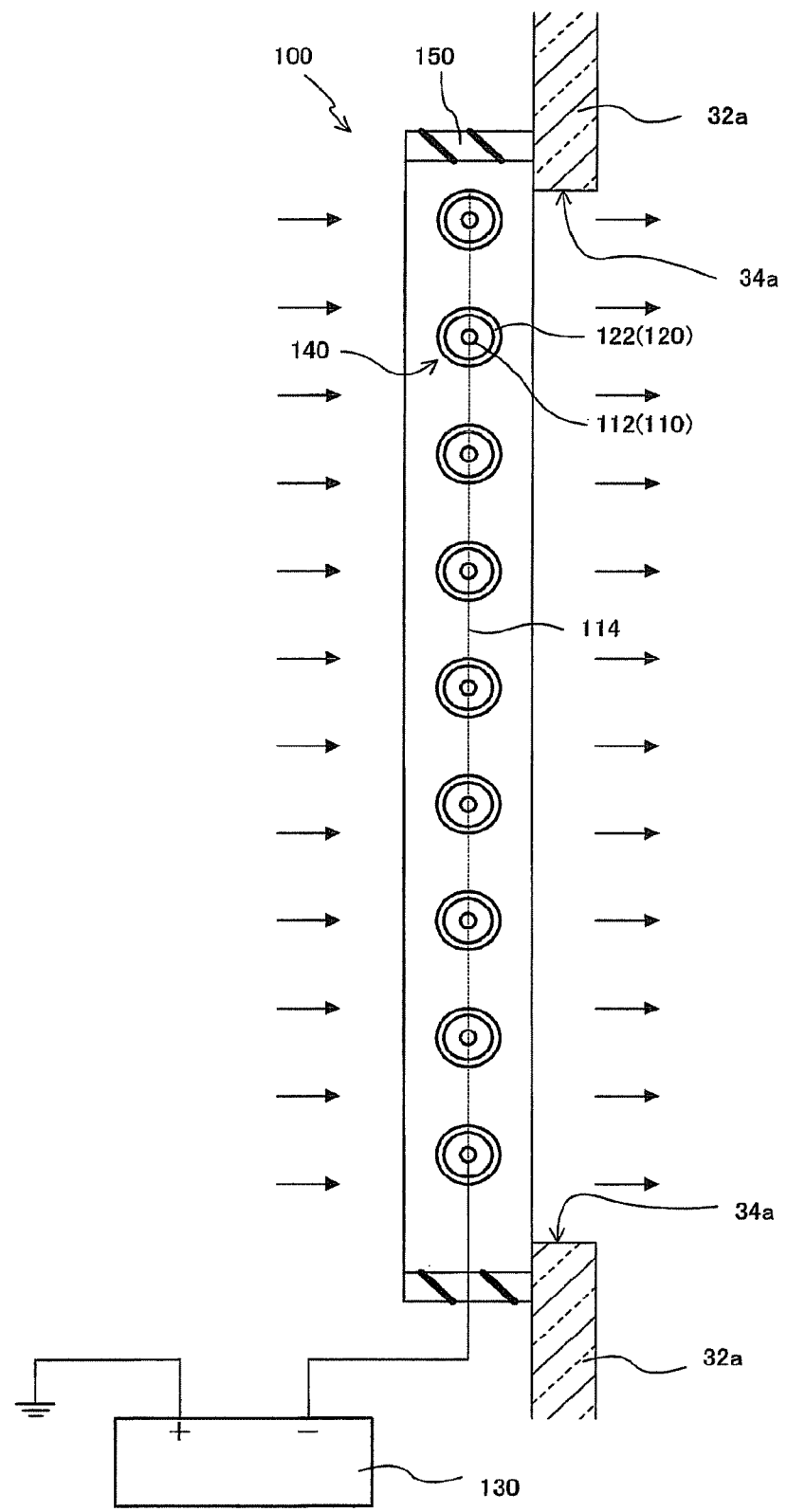

FIG. 6 is a perspective view showing the outline of the flying organism removing apparatus 100, and FIG. 7 is a cross-sectional view showing the outline of the flying organism removing apparatus 100. To clarify the configuration, the flying organism removing apparatus 100 shown in FIG. 6 is simplified by showing a casing 150 to be described later with a broken line. FIG. 7 shows, as one example, that the flying organism removing apparatus 100 is attached to the opening 34a of the front wall 32a of the plant protecting apparatus 15.

The flying organism removing apparatus 100 includes the casing 150, a conductor 110, a dielectric 120, and a power supply 130. As will be described later, the conductor 110 and the dielectric 120 form the dielectric covered conductor 140.

The casing 150 of the flying organism removing apparatus 100 has two side parts 162a and 162b, a ceiling part 164 and a bottom part 166.

The two side parts 162a and 162b have approximately same shapes, and are formed of an approximately rectangular thin plates. The two side parts 162a and 162b are arranged to be separated from and in parallel to each other. The ceiling part 164 and the bottom part 166 have approximately same shapes, and are formed of an approximately rectangular thin plates. The ceiling part 164 and the bottom part 166 are arranged to be separated from and in parallel to each other.

The two side parts 162a and 162b, the ceiling part 164 and the bottom part 166 are formed of a material insulated electrically, for example, transparent plastic. The use of a transparent material for the casing 150 can allow light to be adequately irradiated on plants in the plant protecting apparatus 15 without blocking the light when the flying organism removing apparatus 100 is attached to the plant protecting apparatus 15.

The two side parts 162a and 162b, the ceiling part 164 and the bottom part 166 form a front surface 168a and a rear surface 168b of the flying organism removing apparatus 100. That is, the front surface 168a and the rear surface 168b are formed in an area surrounded by the two side parts 162a and 162b, the ceiling part 164 and the bottom part 166, and each of the front surface 168a and the rear surface 168b is entirely open. The front surface 168a and the rear surface 168b are positioned to face each other, so that air can flow through the front surface 168a and the rear surface 168b. The front surface 168a and the rear surface 168b correspond to the "casing opening".

When the flying organism removing apparatus 100 is attached to the plant protecting apparatus 15, the rear surface 168b of the flying organism removing apparatus 100 is substantially aligned with the openings 34a and 34b of the plant protecting apparatus 15. Therefore, air can flow through the front surface 168a and the rear surface 168b, and the opening 34a of the plant protecting apparatus 15, so that the air can be supplied to the plant protecting apparatus 15 via the flying organism removing apparatus 100. Likewise, air can flow through the front surface 168a and the rear surface 168b, and the opening 34b of the plant protecting apparatus 15, so that the air can be supplied to the plant protecting apparatus 15 via the flying organism removing apparatus 100. The openings 34a and 34b of the plant protecting apparatus 15 correspond to a "ventilation opening."

As shown in FIG. 7, the flying organism removing apparatus 100 is attached to the outer surface of the front wall 32a of the plant protecting apparatus 15 in such a way as to cover the opening 34a formed in the front wall 32a. As mentioned above, when the flying organism removing apparatus 100 is attached to the plant protecting apparatus 15 (not shown), the rear surface 168b of the flying organism removing apparatus 100 is aligned with the opening 34a of the plant protecting apparatus 15. In FIG. 7, the leftward direction in the diagram is the outside of the plant protecting apparatus 15, and the rightward direction in the diagram is the inside of the plant protecting apparatus 15, with the plant arrangement zone 20 (not shown) being present. The arrows shown in FIG. 7 show the flow of the air which flows toward the interior of the plant protecting apparatus 15 from outside thereof via the flying organism removing apparatus 100.

<Conductor 110 (Electric Conductor 112)>

As mentioned above, the flying organism removing apparatus 100 includes the conductor 110. In the flying organism removing apparatus 100 according to the second embodiment, the conductor 110a comprises nine electric conductors 112. Those nine electric conductors 112 form "at least one conductor" and "a plurality of electric conductors".

As shown in FIG. 6 or 7, each of the nine electric conductors 112 has an elongated and approximately linear shape extending straight. Specifically, each of the nine electric conductors 112 has an approximately rod-like shape. In FIG. 7, the cross sections of the nine electric conductors 112 are illustrated. As shown in FIG. 7, the cross-sectional shape of each of the nine electric conductors 112 is approximately circular. The shape of each of the nine electric conductors 112 is not limited to a linear shape, and an electric conductor which can keep a certain shape can be used, and for example, it may have a shape curved along a given curvature.

Each of the nine electric conductors 112 is disposed horizontally (direction perpendicular to the sheet of FIG. 7) between the two side parts 162a and 162b of the casing 150. With the nine electric conductors 112 disposed this way, each of the nine electric conductors 112 becomes an elongated conductive wire horizontally extending straight.

Further, the nine electric conductors 112 are arranged in the perpendicular direction (up and down direction to the sheet of FIG. 7) to be separated from one another, so that there is a predetermined interval between adjoining electric conductors. The nine electric conductors 112, when arranged this way, are disposed along a first plane 114 shown in FIG. 7. The first plane 114 will be described later.

The nine electric conductors 112 are electrically connected to one another by unillustrated electric wires at the two side parts 162a and 162b of the casing 150. This makes the potential of each of the nine electric conductors always the same.

<Dielectric 120 (Dielectric Cover 122)>

As mentioned above, the flying organism removing apparatus 100 includes the dielectric 120. In the flying organism removing apparatus 100 according to the second embodiment, the dielectric 120 comprises nine dielectric covers 122. Those nine dielectric covers 122 form "at least one dielectric" and "a plurality of dielectric covers".

As shown in FIG. 6 or 7, each of the nine dielectric covers 122 has an elongated and approximately cylindrical shape extending straight. In FIG. 7, the cross sections of the nine dielectric covers 122 are illustrated. As shown in FIG. 7, the cross-sectional shape of each of the nine dielectric covers 122 is approximately annular. The shape of each of the nine dielectric covers 122 is not limited to a shape extending straight, and a dielectric cover which can keep a certain shape can be used, and it may have a shape curved along a given curvature.

Each of the nine dielectric covers 122 is disposed horizontally (direction perpendicular to the sheet of FIG. 7) between the two side parts 162a and 162b of the casing 150. One end portion of each of the nine dielectric covers 122 is held by the side part 162a of the casing 150, and the other end portion of each of the nine dielectric covers 122 is held by the side part 162b of the casing 150. This can allow each of the nine dielectric covers 122 to be supported between the two side parts 162a and 162b of the casing 150.

Further, the nine dielectric covers 122 are arranged in the perpendicular direction (up and down direction to the sheet of FIG. 7) to be separated from one another, so that there is a predetermined interval between adjoining dielectric covers. The nine dielectric covers 122, when arranged this way, are disposed along a first plane 114 shown in FIG. 7. The first plane 114 will be described later.

The dielectric 120 is made of a dielectric material. That is, the dielectric 120 may be anything which is not electrically conductive or so-called insulator. Examples of the material for the dielectric include vinyl chloride, polyethylene, polypropylene, urethane, polyester, rayon, cellulose, rubber, or the like. Particularly, it is preferable to use a material which makes the dielectric 120 transparent. Making the dielectric 120 transparent can allow light to be adequately irradiated on plants in the plant protecting apparatus 15 without blocking the light when the flying organism removing apparatus 100 is attached to the plant protecting apparatus 15, as shown in FIG. 7. The dielectric 120, even if not transparent, preferably transmits 50% or more of light, and is disposed in such a way that when it is attached to the plant protecting apparatus 15, the transmittance at the entire opening 34a of the front wall 32a of the plant protecting apparatus 15 becomes 50% or greater. Further, when the dielectric 120 is not transparent, it is preferable to adjust the transmittance of light at the entire opening 34a of the front wall 32a of the plant protecting apparatus 15 by the number and thickness of the dielectric covers 122.

<Dielectric Covered Conductor 140>

As described above, the dielectric covered conductor 140 comprises the conductor 110 and the dielectric 120. Specifically, one dielectric covered conductor 140 comprises one conductor 112 and one dielectric cover 122. That is, the flying organism removing apparatus 100 according to the second embodiment is configured in such a way that one conductor 112 and one dielectric cover 122 make a pair.

Figure 8:
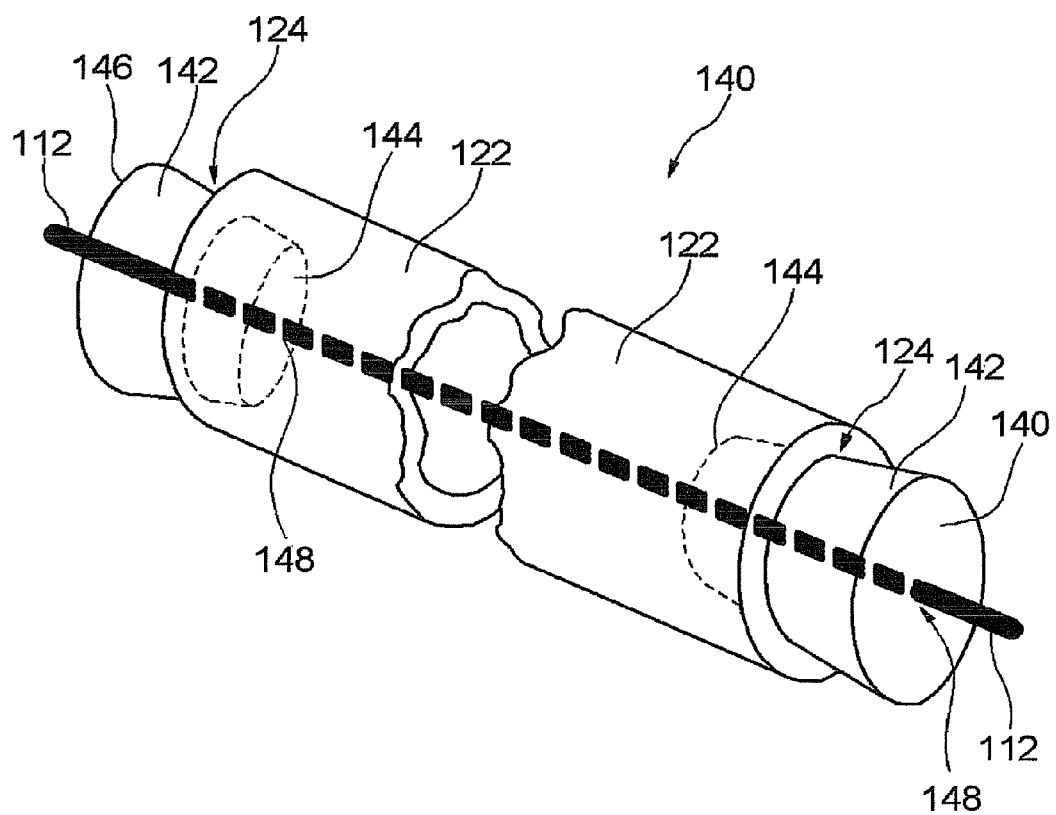
Figure 9:
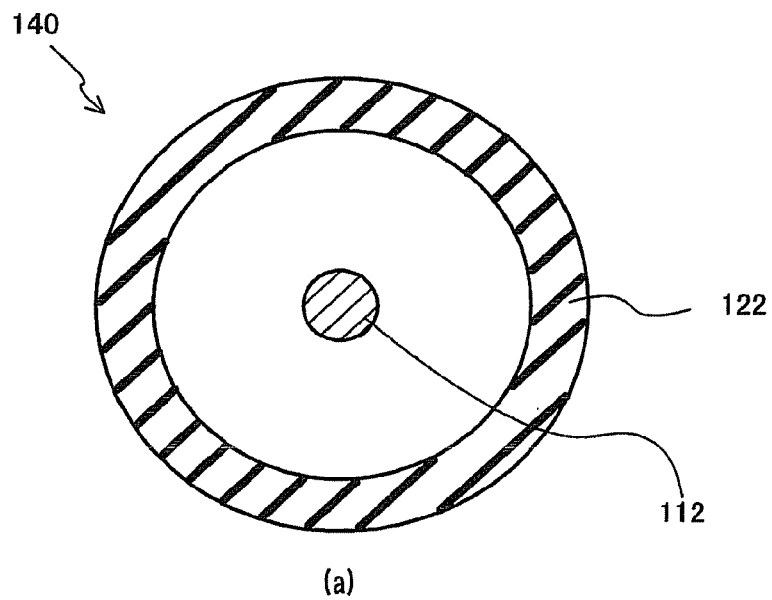
Figure 9:
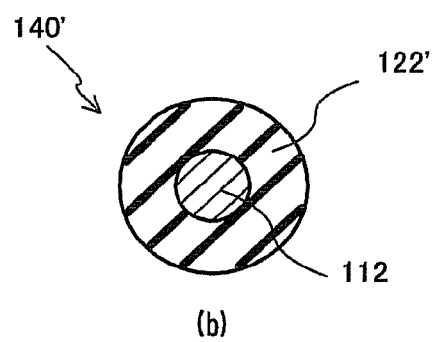

FIG. 8 is a perspective view showing the structure of one dielectric covered conductor 140. FIG. 9(*a*) is a cross-sectional view showing the structure of one dielectric covered conductor 140.

One dielectric covered conductor 140 includes one conductor 112, one dielectric cover 122, and two support members 142.

As described above, the dielectric cover 122 has an elongated and approximately cylindrical shape extending straight. That is, an elongated space along the axial direction is formed inside the dielectric cover 122. Approximately circular openings 124 are formed at both ends of the dielectric cover 122.

As shown in FIG. 8, the aforementioned one electric conductor 112 is laid out on the elongated space, formed inside the dielectric cover 122, along the longitudinal direction of the dielectric cover 122.

The support members 142 for supporting the electric conductor 112 are provided at the openings 124 at both ends of the dielectric cover 122. The support member 142 has an approximately circular truncated cone shape having two end faces, a first end face 144 and a second end face 146. The first end face 144 and second end face 146 of the support member 142 have approximately circular shapes. The support member 142 is formed in such a way that the diameter of the first end face 144 becomes smaller than the diameter of the dielectric cover 122, and the diameter of the second end face 146 becomes larger than the diameter of the dielectric cover 122. A through hole 148 is formed in the support member 142 in such a way as to pass near the center of the first end face 144 and near the center of the second end face 146 along the center axial direction of the support member 142. The through hole 148 is formed in such a way that the diameter of the through hole 148 becomes slightly smaller than the diameter of the electric conductor 112. The support member 142 is made of an elastic member, such as rubber, so that it can be deformed slightly.

As shown in FIG. 8, the electric conductor 112 put through the through hole 148 of the support member 142 is supported on the support member 142 by the elastic force of the support member 142. As the first end faces 144 of the support members 142 are pushed into the two openings 124 of the dielectric cover 122, the support members 142 are secured to the two openings 124 by the elastic force of the support members 142. This can allow the electric conductor 112 to be disposed and held in the elongated space formed inside the dielectric cover 122 along the longitudinal direction thereof, as shown in FIGS. 8 and 9(*a*). Specifically, the electric conductor 112 is disposed and held in the dielectric cover 122 so as to be along the axial center of the dielectric cover 122 and separated from the dielectric cover 122.

With this configuration, the electric conductor 112 can be covered with the dielectric cover 122. As shown in FIG. 6 or FIG. 7, one electric conductor 112 is disposed in each of the nine dielectric covers 122 in the same way, thus forming the nine dielectric covered conductors 140.

Such a shape can make the nine dielectric covered conductors 140 smaller with respect to the perpendicular direction, and make the surface area larger. As they can be made thinner in the perpendicular direction, the thickness of the flying organism removing apparatus 100 (length in the right and left direction in FIG. 7) can be made thinner. When the nine dielectric covers 122 are formed of a transparent material, as described above, light can be adequately irradiated on plants in the plant protecting apparatus 15 without blocking the light when the flying organism removing apparatus 100 is attached to the plant protecting apparatus 15.

With the nine dielectric covered conductors 140 formed into such a shape, it is possible to bend the flow of the air, rotate the air or produce air vortex by the outer surfaces of the nine dielectric covered conductors 140 when air is supplied to plants via the flying organism removing apparatus 100. It is possible to increase the chance for making flyable organisms present in the area where an electric field generated by the dielectric polarization of the nine dielectric covered conductors 140 is effectively present by bending the air flow or giving a rotational component to air flow, thereby the flyable organisms can be captured adequately.

Further, as the nine dielectric cover 122 are arranged in the perpendicular direction (up and down direction to the sheet of FIG. 7) to be separated from one another, with a predetermined interval provided between adjoining dielectric cover, so that the nine dielectric covered conductors 140 are arranged to be separated from one another in the perpendicular direction, as shown in FIG. 6 or FIG. 7. That is, the nine dielectric covered conductors 140 are arranged in a so-called rattan blind pattern, so that a clearance is produced between the adjoining dielectric covered conductors 140. This can allow air to be sufficiently supplied to the plant protecting apparatus 15 via the clearances formed between the adjoining dielectric covered conductors 140, and can allow light to be irradiated on plants placed in the plant protecting apparatus 15 through the clearances. Further, when the nine dielectric covers 122 are made of a transparent member, as mentioned above, light can be irradiated on plants placed in the plant protecting apparatus 15 through the nine dielectric covers 122 as well as the clearances formed between the dielectric covered conductors 140.

The thickness of each of the nine dielectric covers 122 and the interval between the adjoining dielectric covers 122 may be properly set according to the voltage to be applied to the electric conductor 112, the amount of air passing through the flying organism removing apparatus 100, and so forth.

When the dielectric cover 122 and the electric conductor 112 are set apart, as shown in FIG. 8 and FIG. 9(*a*), i.e., when the dielectric cover 122 is not in direct contact with the electric conductor 112, it is preferable that, for example, the dielectric cover 122 should be made to be an acrylic cylinder and the thickness of the dielectric cover 122 should be equal to 10 cm or less. It is more preferable that the thickness of the dielectric cover 122 should be equal to 6 cm or less, and it is further preferable that the thickness of the dielectric cover 122 should be equal to 4 cm or less. Meanwhile, the electric conductor 112 has only to be arranged at a position where dielectric polarization of the dielectric cover 122 can be effected. That is, the thickness of the electric conductor 112 disposed inside the dielectric cover 122 can be determined according to the thickness of the dielectric cover 122. The electric conductor 112 may be a solid copper wire or copper pipe.

The interval between the adjoining dielectric covers 122 may be properly set according to the voltage to be applied to the electric conductor 112, the thickness of the dielectric cover 122, the amount of air passing through the flying organism removing apparatus 100, and so forth. For example, the interval between the adjoining dielectric covers 122 is preferably 10 cm or less, is more preferably 8 cm or less, and is further preferably 6 cm or less.

<First Plane 114>

A scheme of specifying the first plane 114 will be described below.

To begin with, the shape of each of the nine dielectric covered conductors 140 is specified by the shape of one line. One line for the dielectric covered conductors 140 can be set by setting the centers of the dielectric covered conductors 140 on a plane perpendicular to the longitudinal direction of one dielectric covered conductor 140, and connecting the centers along the longitudinal direction of the dielectric covered conductors 140. Lines characterizing the nine dielectric covered conductors 140 can be set one by one. In the first embodiment, each of the nine dielectric covered conductors 140 has a shape extending straight as mentioned above, the line characterizing each of the nine dielectric covered conductors 140 also becomes straight.

In the next place, the first plane 114 can be set by specifying a plane almost containing the lines characterizing the shapes of the nine dielectric covered conductors 140. In specifying the first plane 114, a strict plane which always contains all of the lines need not be assumed, and a plane which almost contains the lines should be set as the first plane 114. It is noted that because the line characterizing the shape of each of the nine dielectric covered conductors 140 is straight as mentioned above in the first embodiment, the shape of the first plane 114 becomes a single flat surface.

Although FIG. 7 exemplifies a case where the first plane 114 characterizing the general shape of the nine dielectric covered conductors 140 is a flat surface, the first plane 114 is not limited to a flat surface, and may be a curved surface. The nine dielectric covered conductors 140 may be disposed along a given surface.

The outer sides of the nine dielectric covered conductors 140 are defined by the nine dielectric covers 122, so that even if the first plane is specified by the nine dielectric covers 122, it matches with the first plane 114.

With the electric conductor 112 being disposed along the axial line of the dielectric covered conductor 140, even if the first plane is specified by the nine electric conductors 112, it also matches with the first plane 114.

<Power Supply 130>

The power supply 130 has a positive terminal and a negative terminal which can output a predetermined DC voltage.

Each of the nine electric conductors 112 constituting the conductor 110 is connected to the negative terminal of the power supply 130. In the first embodiment, the positive terminal of the power supply 130 is grounded.

The DC voltage to be applied to the nine electric conductors 112 should be properly set according to the interval between the nine electric conductors 112, the material of the nine dielectric covers 122, the amount of air passing between the nine dielectric covers 122, and so forth. For example, any voltage enough to apply a high voltage to flyable organism, such as disease and vermin, and capture the flyable organism will be applicable. Specifically, the DC voltage to be applied to the nine electric conductors 112 is preferably 1 to 40 kV, is more preferably 3 to 30 kV, and is further preferably 5 to 20 kV. When the DC voltage to be applied is 1 to 40 kV, it is possible to adequately eliminate flyable organism between the first conductor and the second conductor. When the DC voltage to be applied is too low, on the other hand, dielectric polarization of flyable organism may not be effected, which is not preferable.

An electrostatic field can be generated around the nine electric conductors 112 by applying a DC voltage to the nine electric conductors 112. As described above, each of the nine electric conductors 112 is covered with the dielectric cover 122. Accordingly, the electrostatic field produced from the nine electric conductors 112 can cause dielectric polarization in and at the nine dielectric covers 122. The dielectric polarization caused at the nine dielectric covers 122 can further generate an electric field around the nine dielectric covers 122. Since the dielectric cover 122 has an approximately cylindrical shape, the electric field produced around the nine dielectric covers 122 becomes an electric field (non-uniform electric field, uneven field) whose field intensity differs according to the position. With such an electric field generated, when flyable organisms are charged, the Coulomb force can be exerted on the flyable organisms, and when the flyable organisms are electrically neutral, electric static induction can be produced at the flyable organism, so that gradient force can be exerted on the flyable organisms. The generation of such an electric field allows the Coulomb force or the gradient force to be exerted on flyable organisms, thus making it difficult for the flyable organisms to move. Accordingly, an electric field generated by the dielectric polarization of the nine dielectric covers 122 forms an electrostatic screen which can adequately capture flyable organisms.

In the second embodiment, a DC high voltage generating device is used as the power supply 130. This can apply a constant high voltage to the conductor 110, so that an electric field generated around the nine dielectric covers 122 can capture and prevent flyable organisms from entering the plant arrangement zone 20 of the plant protecting apparatus 15.

The plant protecting apparatus 15 may be ventilated naturally or forcibly. In case of the forced ventilation, the wind speed may be properly set according to the interval between the nine dielectric covered conductors 140, the voltage to be applied to the electric conductor 112, the diameter of the nine dielectric covers 122, and so forth. One example is 1 to 600 $m^3$/min per 1 $m^2$ for the openings 34a and 34b of the plant protecting apparatus 15.

<Dielectric Covered Conductor 140'>

FIG. 9(a) as mentioned above shows the dielectric covered conductor 140 having the electric conductor 112 disposed inside the dielectric cover 122 in such a way that the dielectric cover 122 and the electric conductor 112 are separated from each other.

On the other hand, as shown in FIG. 9(b), a dielectric covered conductor 140' having the electric conductor 112 disposed in the dielectric cover 122' so that the dielectric cover 122' is in close contact with the electric conductor 112 may be used. Accordingly, the diameter of the dielectric covered conductor 140' can be made thinner, so that the thickness of the flying organism removing apparatus 100 (length in the right and left direction in FIG. 7) can be made smaller. As the radius of curvature of the outer surface of the dielectric covered conductor 140' can be made large, the rate of the positional change of the electrostatic field, produced by the dielectric covered conductor 140' can be made larger. This can make the gradient force greater, thus making it possible to capture flyable organisms more easily.

As a mode of making the dielectric cover 122' and the electric conductor 112 in close contact with each other, a covered copper wire to be used in electric wiring, there are a covered copper plate covered with a dielectric material, or the like.

The thickness of each of the nine dielectric covers 122' and the interval between the adjoining dielectric covers 122 may be properly set according to the voltage to be applied to the electric conductor 112, the amount of air passing through the flying organism removing apparatus 100, and so forth.

When the dielectric cover 122' and the electric conductor 112 are in close contact with each other, as shown in FIG. 9(b), i.e., when the dielectric cover 122' is in direct contact with the electric conductor 112, it is preferable that, for example, the dielectric covered conductor 140' should be a vinyl chloride covered copper wire whose thickness is equal to 10 mm or less. The thickness of the dielectric covered conductor 140' is more preferably equal to 6 mm or less, and is further preferably 4 mm or less. Meanwhile, the thickness of the electric conductor 112 disposed inside the dielectric cover 122' can be determined according to the thickness of the dielectric cover 122'.

The interval between the adjoining dielectric covers 122' may be properly set according to the voltage to be applied to the electric conductor 112, the thickness of the dielectric cover 122', the amount of air passing through the flying organism removing apparatus 100, and so forth. For example, the interval between the adjoining dielectric covers 122' is preferably 6 cm or less, is more preferably 4 cm or less, and is further preferably 2 cm or less. The reason for making the interval between the adjoining dielectric covers 122' closer as compared with the case where the dielectric cover is not in direct contact with the electric conductor 112 is that the diameter of the dielectric cover 122' tends to become smaller when the dielectric cover 122' is in direct contact with the electric conductor 112. Thereby the interval can be made smaller accordingly, and an electric field produced by the dielectric polarization of the dielectric cover 122' can be allowed to effectively exist between the adjoining dielectric covers 122'.

<Dielectric Cover 222, 322, 422>

Figure 10:
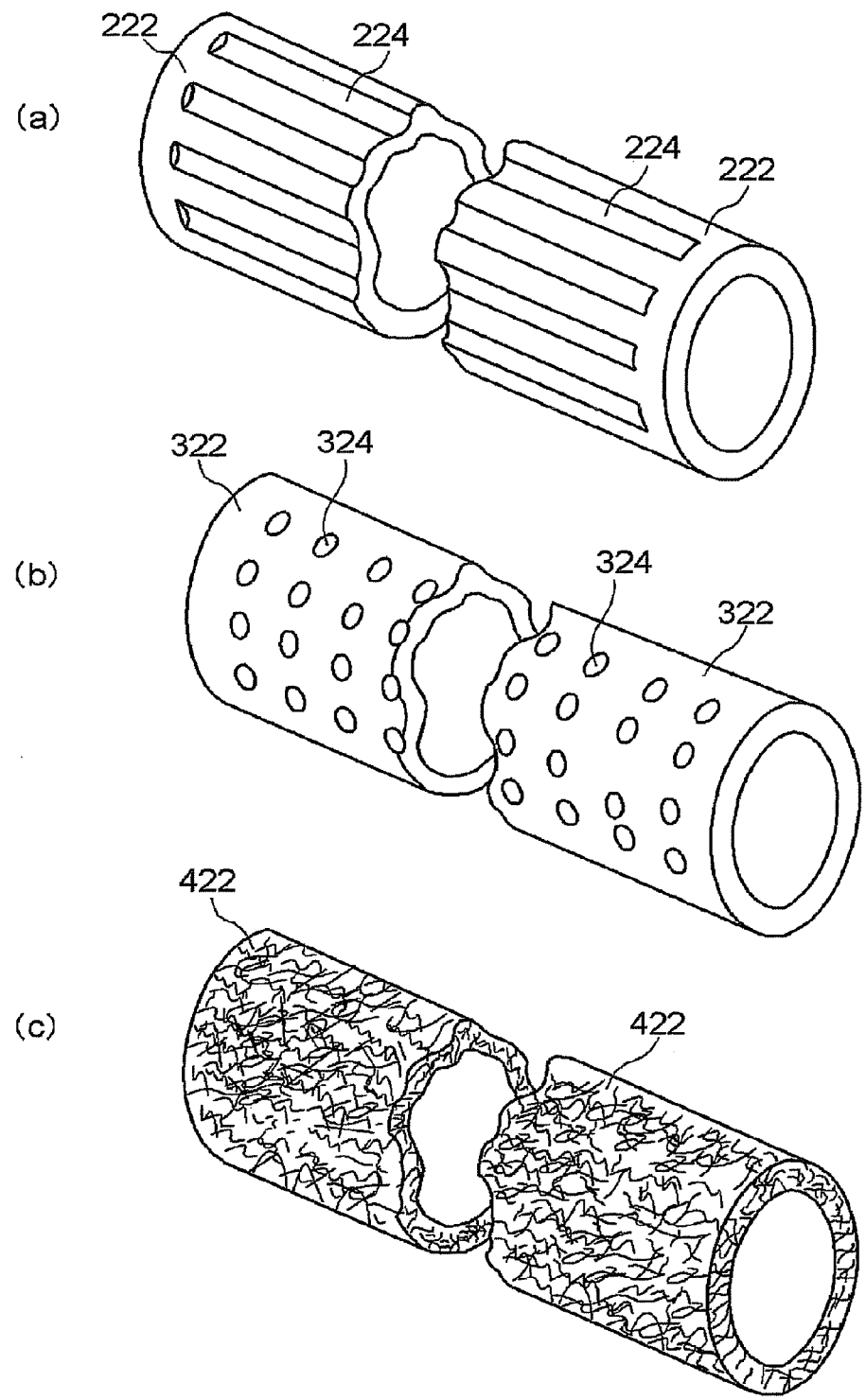

FIG. 10(a) to FIG. 10(c) are perspective views showing second to fourth examples of the dielectric cover. The electric conductor 112 and two support members 142 are omitted in FIG. 10(a) to FIG. 10(c).

A dielectric cover 222 of the second example shown in FIG. 10(a), a dielectric cover 322 of the third example shown in FIG. 10(b), and a dielectric cover 422 of the fourth example shown in FIG. 10(c), like the dielectric cover 122 of the first example, have generally elongated and approximately cylindrical shapes extending straight.

A plurality of grooves 224 are formed in the outer surface of the dielectric cover 222 of the second example. A plurality of recesses or through holes 324 are formed in the outer surface of the dielectric cover 322 of the third example. In the case of the dielectric cover 322 of the third example, not only recesses but also through holes may be formed. In case of forming through holes, it is preferable that the distance to the adjoining electric conductors 112 and the voltage to be applied should be set so that the electric conductor 112 disposed inside does not cause discharge.

Forming such groves 224 or such recesses or through holes 324 in the outer surface can make more uneven the intensity of the electric field produced by the dielectric polarization of the nine dielectric covers 222 or 322. The production of such an electric field can allow a greater gradient force to be exerted on flyable organisms, thus making the movement of the flyable organisms harder and making it possible to capture the flyable organisms.

The groves 224 or the recesses or through holes 324 can bend the flow of air flowing near the outer surface of the dielectric cover 222 or 322 more, or rotate the air more or make it easier to produce an air vortex. This can increases the chance of capturing flyable organisms which will enter the plant arrangement zone from the opening.

Further, the dielectric cover 422 shown in FIG. 10(c) is molded of a dielectric fibrous material. Even if such configuration is taken, it can produce an electric field which has a more uneven intensity, so that a greater gradient force can be exerted on flyable organisms, thus making the movement of the flyable organisms harder and enabling to catch the flyable organisms.

The use of the fibrous material can make the flow of air better, can bend the flow of air more, or rotate the air more or produce an air vortex more.

Although the flying organism removing apparatus 100 is illustrated to have each of the nine dielectric covered conductors 140 disposed in the horizontal direction, a plurality of dielectric covered conductors 140 may be disposed so as to be able to irradiate light on plants placed in the plant arrangement zone 20 and supply air thereto, and may be disposed perpendicularly or obliquely as well as horizontally.

Third Embodiment

Flying Organism Removing Apparatus 200

Figure 11:
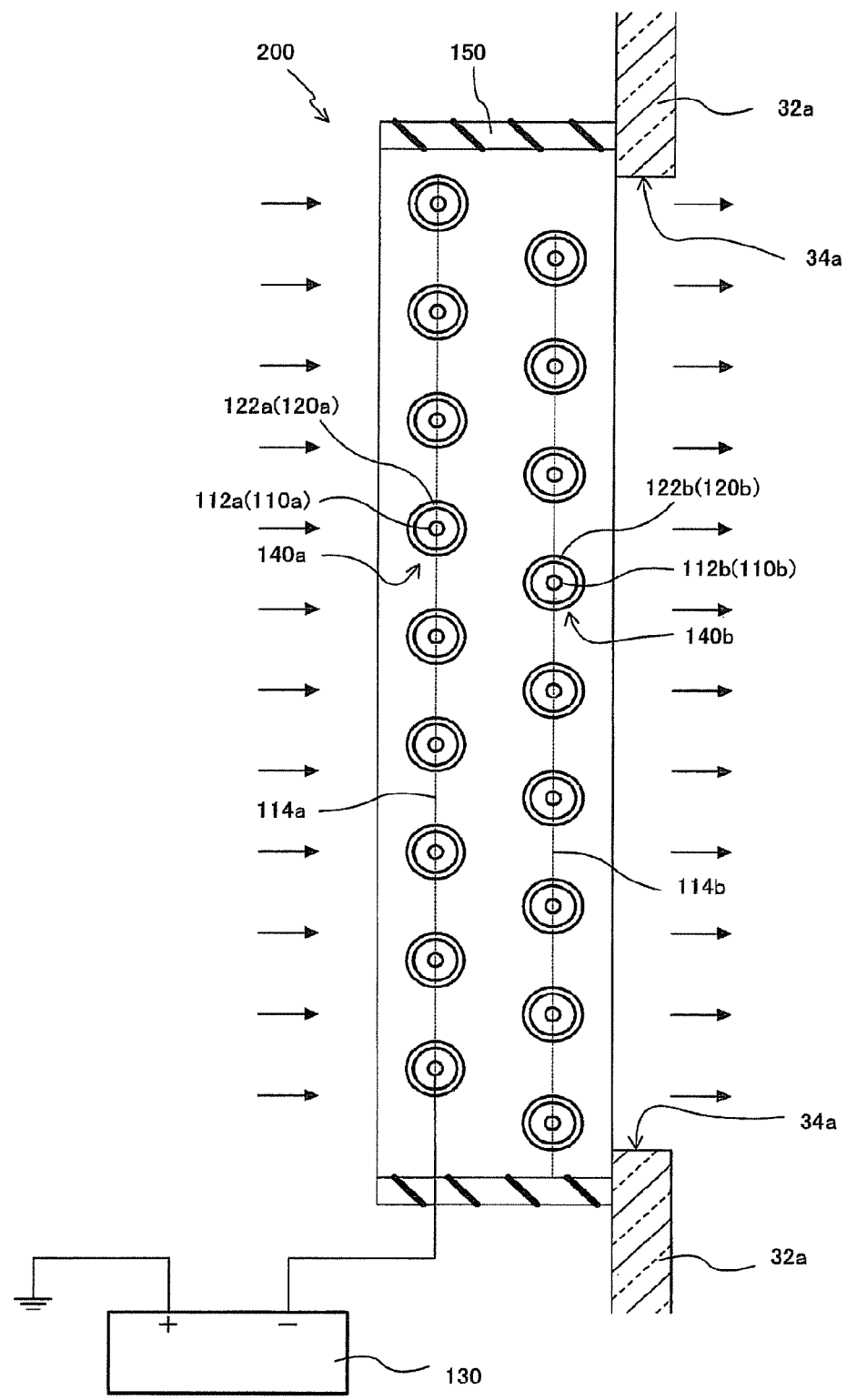

FIG. 11 is a cross-sectional view showing the outline of the flying organism removing apparatus 200. FIG. 11 shows, as one example, that the flying organism removing apparatus 200 is attached to the opening 34a of the front wall 32a of the plant protecting apparatus 15.

The flying organism removing apparatus 200 includes a casing 150, conductors 110a and 110b, dielectrics 120a and 120b, and a power supply 130. As will be described later, the conductor 110a and the dielectric 120a form a dielectric covered conductor 140a, and the conductor 110b and the dielectric 120b form a dielectric covered conductor 140b.

The casing 150 and the power supply 130 have structures and functions similar to the structures and functions of those of the flying organism removing apparatus 100, so that their descriptions will be omitted.

<Conductor 110a, 110b>

As mentioned above, the flying organism removing apparatus 200 includes the conductors 110a and 110b. The conductor 110a comprises nine electric conductors 112a. The conductor 110b comprises nine electric conductors 112b. Those nine electric conductors 112a, 112b have a structure similar to that of the nine electric conductors 112 of the flying organism removing apparatus 100. The nine electric conductors 112a, 112b are electrically connected to the power supply 130. The nine electric conductors 112a, 112b form "at least one conductor" and "a plurality of electric conductors".

<Dielectric 120a, 120b>

As mentioned above, the flying organism removing apparatus 200 includes the dielectrics 120a and 120b. The dielectric 120a comprises nine dielectric covers 122a. The dielectric 120b comprises nine dielectric covers 122b. Those nine dielectric covers 122a, 122b have a structure similar to that of the nine dielectric covers 122 of the flying organism removing apparatus 100. The nine dielectric covers 122a, 122b form "at least one dielectric" and "a plurality of dielectric covers".

<Dielectric Covered Conductor 140a, 140b>

The nine electric conductors 112a and the nine dielectric covers 122a form nine dielectric covered conductors 140a, and the nine electric conductors 112b and the nine dielectric covers 122b form nine dielectric covered conductors 140b. Therefore, each of the nine dielectric covered conductors 140a, 140b has a structure similar to that of the nine dielectric covered conductors 140 of the flying organism removing apparatus 100.

The nine dielectric covered conductors 140a, and the nine dielectric covered conductors 140b, as well as the nine dielectric covered conductors 140 of the flying organism removing apparatus 100, are disposed to be separated from one another in the perpendicular direction. That is, the nine dielectric covered conductors 140a are disposed in a so-called rattan blind pattern so that a clearance is provided between the adjoining two dielectric covered conductors 140a. Likewise, the nine dielectric covered conductors 140b are disposed in a so-called rattan blind pattern so that a clearance is provided between the adjoining two dielectric covered conductors 140b.

The nine dielectric covered conductors 140a form one "dielectric covered conductor group", and the nine dielectric covered conductors 140b form one "dielectric covered conductor group". Particularly, the nine dielectric covered conductors 140a form the "first dielectric covered conductor group", and the nine dielectric covered conductors 140b form the "second dielectric covered conductor group".

One dielectric covered conductor 140a comprises one electric conductor 112a and one dielectric cover 122a. That is, the flying organism removing apparatus 200 is configured so that one dielectric cover 122a and one electric conductor 112a make a pair. Likewise, one dielectric covered conductor 140b comprises one electric conductor 112b and one dielectric cover 122b. That is, the flying organism removing apparatus 200 is configured so that one dielectric cover 122b and one electric conductor 112b make a pair.

With regard to the vertical (up and down direction to the sheet of FIG. 11) layout of the flying organism removing apparatus 200, as shown in FIG. 11, it is preferable that one of the nine dielectric covered conductors 140b should be disposed between adjoining ones of the nine dielectric covered conductors 140a or in a so-called alternate layout. When the nine dielectric covered conductors 140b become the reference, the alternative layout is preferable so that one of the nine dielectric covered conductors 140a can be disposed between adjoining ones of the nine dielectric covered conductors 140b.

This layout can allow an electric field to be produced around the nine dielectric covers 122a, 122b by the dielectric polarization caused at the nine dielectric covers 122a, 122b, so that the range of generating the electric field can be made wider. Accordingly, a first electrostatic screen can be formed by the dielectric polarization caused at the nine dielectric covers 122a, and a second electrostatic screen can be formed by the dielectric polarization caused at the nine dielectric covers 122b, and the two electrostatic screens can capture flyable organisms more adequately.

Although the flying organism removing apparatus 200 is illustrated to have two "dielectric covered conductor groups" formed by the nine dielectric covered conductors 140a and 140h, which is not restrictive, three "dielectric covered conductor groups" or more may be formed. This can form three or more electrostatic screens to be able to capture flyable organisms more adequately.

Although the flying organism removing apparatus 200 is illustrated to have each of the nine dielectric covered conductors 140a, 140b disposed horizontally, a plurality of dielectric covered conductors 140a, 140b may be disposed in any way as to permit light to be irradiated on plants placed in the plant arrangement zone 20 and supply air to the plants, and may be disposed perpendicularly or obliquely as well as horizontally. The nine dielectric covered conductors 140a and the nine dielectric covered conductors 140b may be disposed in different directions, so that the nine dielectric covered conductors 140a are disposed horizontally, and the nine dielectric covered conductors 140b are disposed perpendicularly.

FIG. 11 shows a first plane 114a characterizing the general shape of the nine dielectric covered conductors 140a, and a first plane 114b characterizing the general shape of the nine dielectric covered conductors 140b by broken lines. The first planes 114a and 114b can be specified by a scheme similar to that of the flying organism removing apparatus 200.

The outer sides of the nine dielectric covered conductors 140a are defined by the nine dielectric covers 122a, so that even if the first plane is specified by the nine dielectric covers 122a, it matches with the first plane 114a. The same can be applied to the nine dielectric covers 122b.

When the electric conductor 112a is disposed along the axial line of the dielectric covered conductor 140a, it also matches with the first plane 114a even if the first plane is specified by the nine electric conductors 112a. The same can be applicable to the electric conductors 112b.

The interval between the first planes 114a and 114b may be properly set according to the voltage to be applied to the electric conductor 112, the thickness of the dielectric cover 122, the amount of air passing through the flying organism removing apparatus 100, and so forth. For example, the interval between the adjoining dielectric covers 122a and 122b is preferably 10 cm or less, is more preferably 8 cm or less, and is further preferably 6 cm or less. Specifically, the interval between predetermined two adjoining dielectric covers 122a, and the dielectric cover 122b that is closest thereto is preferably set to 10 cm or less, is more preferably set to 8 cm or less, and is most preferably set to 6 cm or less.

Fourth Embodiment

Flying Organism Removing Apparatus 300

Figure 12:
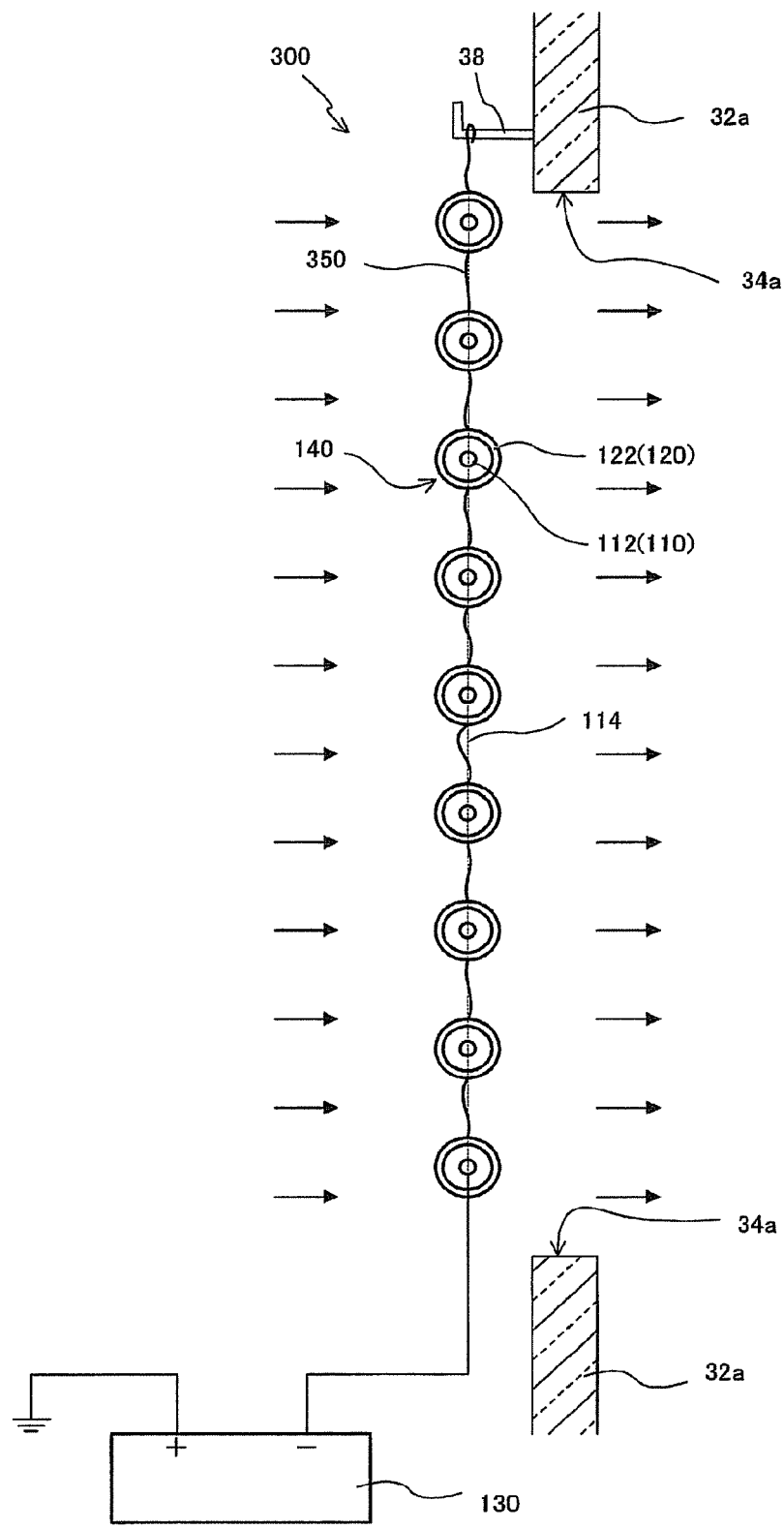

FIG. 12 is a cross-sectional view showing the outline of the flying organism removing apparatus 300. FIG. 12 shows, as one example, that the flying organism removing apparatus 300 is attached to the opening 34a of the front wall 32a of the plant protecting apparatus 15.

The flying organism removing apparatus 300 includes a support 350, conductors 110, dielectrics 120, and a power supply 130. The conductors 110, the dielectrics 120, and the power supply 130 have structures and functions similar to the structures and functions of those of the flying organism removing apparatus 100, so that their descriptions will be omitted. The flying organism removing apparatus 300 is similar to the flying organism removing apparatus 100 in that the conductors 110 and the dielectrics 120 form nine dielectric covered conductors 140. That is, the nine dielectric covered conductors 140 are disposed in a so-called rattan blind pattern so that a clearance is provided between the adjoining two dielectric covered conductors 140.

<Support 350>

The support 350 supports the nine dielectric covered conductors 140. The support 350 is a flexible elongated medium, such as a thread, a line or a wire. The upper end portion of the support 350 is engaged with a hook 38 fixed to the front wall 32a. This allows the nine dielectric covered conductors 140 to be supported like a rattan blind.

Even if such configuration is taken, an electrostatic screen can be formed by an electric field generated by the dielectric polarization of the nine dielectric covers 122 that form the nine dielectric covered conductors 140, and flyable organisms can adequately be captured by the electrostatic screen.

As the support 350 is flexible, the flying organism removing apparatus 300 can be rolled or folded, and can thus be stored easily, and attached and detached easily. Further, at the time of attaching the flying organism removing apparatus 300 to the opening 34a of the front wall 32a of the plant protecting apparatus 15, the nine dielectric covered conductors 140 can be disposed to be aligned with the contour of the opening 34a of the front wall 32a of the plant protecting apparatus 15. Particularly, when it rains or there is a gale, it is possible to prevent drops of water from being put on the flying organism removing apparatus 300 or prevent conidia or small creatures from passing through the flying organism removing apparatus 300 by putting away the flying organism removing apparatus 300 attached to the plant protecting apparatus 15 and closing the opening 34a of the front wall 32a.

FIG. 12 shows the first plane 114 characterizing the general shape of the nine dielectric covered conductors 140. The first plane 114 can be specified by a scheme similar to that of the flying organism removing apparatus 200.

Fifth Embodiment

Flying Organism Removing Apparatus 400

Figure 13:
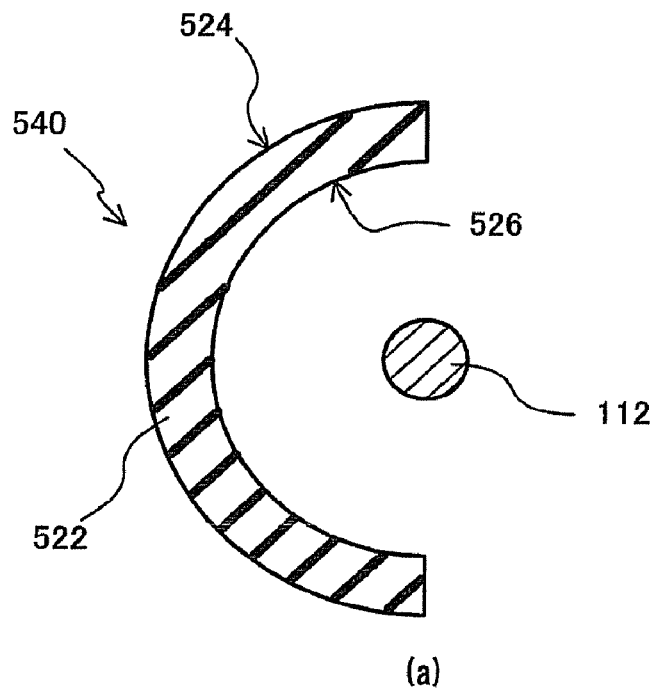
Figure 13:
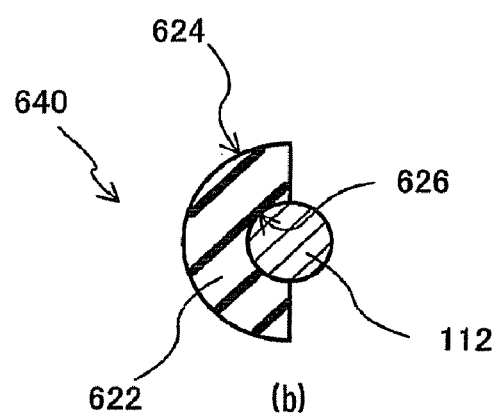

Although the dielectric cover of the dielectric covered conductor used in the flying organism removing apparatus 100, 200 or 300 covers the electric conductor 112 entirely, as shown in FIG. 9, the dielectric cover may cover only a part of the electric conductor 112. FIG. 13 is a cross-sectional view of the dielectric covered conductor showing that example.

FIG. 13(a) is a cross-sectional view of the cross section of one dielectric covered conductor 540 on a plane perpendicular to the elongating direction thereof. One dielectric covered conductor 540 includes one electric conductor 112 and one dielectric cover 522. The electric conductor 112 is similar to that of the foregoing flying organism removing apparatus 100, 200 or 300. The dielectric cover 522 has an elongated approximately semicylindrical shape. In the specification, "approximately semicylindrical" is a half of an approximately cylindrical shape which is formed when nearly bisected at a plane including the axial center line.

The dielectric cover 522 includes an outer surface 524 positioned outside the dielectric cover 522 and an inner surface 526 positioned inside the dielectric cover 522.

The electric conductor 112 is disposed on the inner surface 526 side of the dielectric cover 522 along the longitudinal direction, thus forming the dielectric covered conductor 540. As the dielectric cover 522 of the dielectric covered conductor 540 is made to have an approximately semicylindrical shape, nearly a half of the electric conductor 112 is covered with the dielectric cover 522. A support member (not shown) made of a dielectric material is provided between the dielectric cover 522 and the electric conductor 112. This can allow the dielectric cover 522 to be positioned at a position separate from the electric conductor 112.

FIG. 13(b) is a cross-sectional view of the cross section of one dielectric covered conductor 640 on a plane perpendicular to the elongating direction thereof. One dielectric covered conductor 640 includes one electric conductor 112 and one dielectric cover 622. The electric conductor 112 is similar to that of the foregoing flying organism removing apparatus 100, 200 or 300. The dielectric cover 622 has an elongated approximately semicylindrical shape.

The dielectric cover 622 includes an outer surface 624 positioned outside the dielectric cover 622 and an inner surface 626 positioned inside the dielectric cover 622.

The electric conductor 112 is disposed on the inner surface 626 side of the dielectric cover 622 along the longitudinal direction, thus forming the dielectric covered conductor 640. As the dielectric cover 622 of the dielectric covered conductor 640 is made to have an approximately semicylindrical shape, nearly a half of the electric conductor 112 is covered with the dielectric cover 622. The dielectric cover 622 is positioned to be in close contact with the electric conductor 112.

A plurality of grooves 224 shown in FIG. 10(a) or a plurality of recesses or through holes 324 may be formed in the dielectric cover 522 shown in FIG. 13(a) or in the dielectric cover 622 shown in FIG. 13(b). Further, the dielectric cover 522 shown in FIG. 13(a) or dielectric cover 622 shown in FIG. 13(b) may be molded of a dielectric fibrous material shown in FIG. 10(c).

Figure 14:
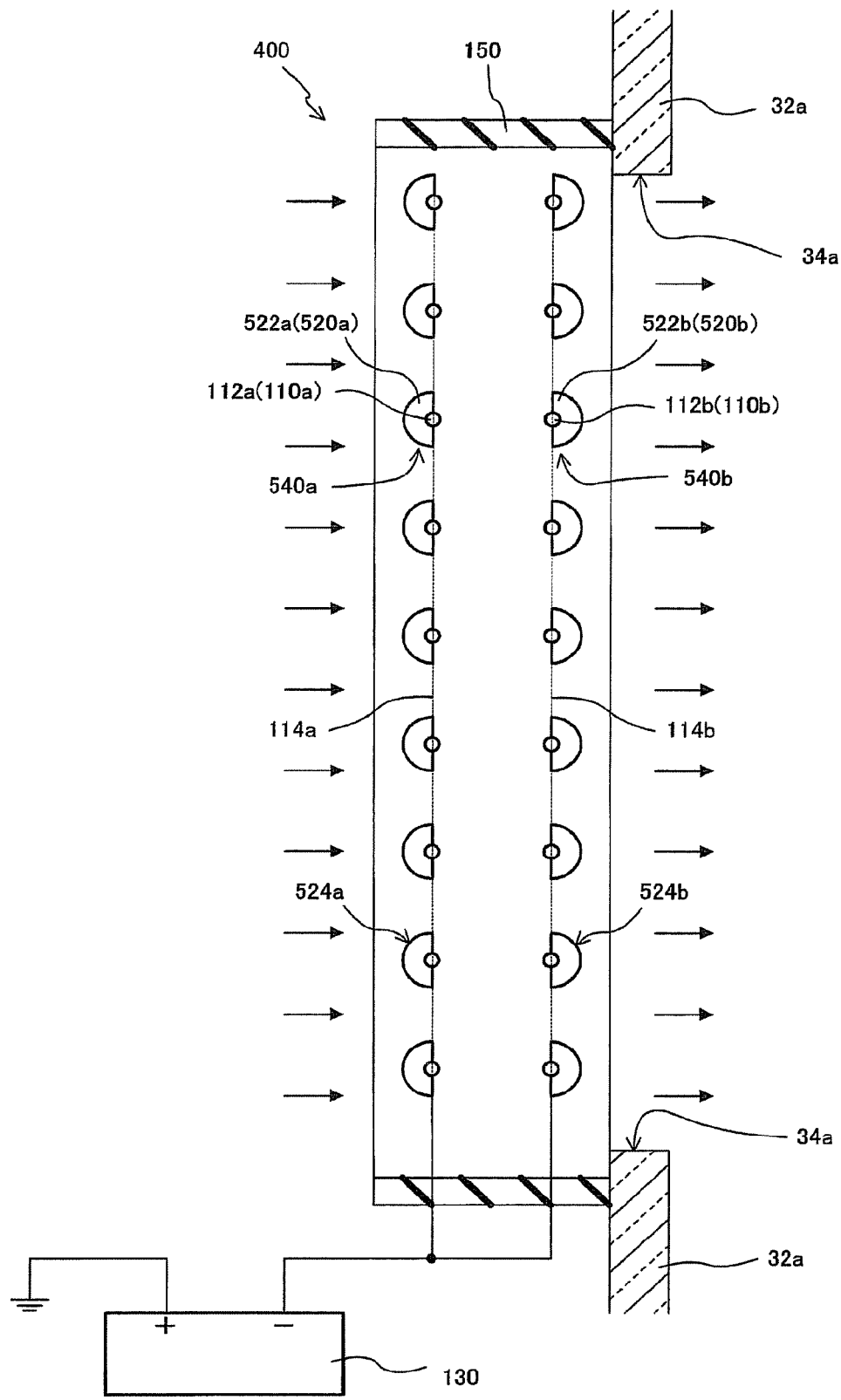

FIG. 14 is a cross-sectional view showing the outline of the flying organism removing apparatus 400. FIG. 14 shows, as one example, that the flying organism removing apparatus 400 is attached to the opening 34a of the front wall 32a of the plant protecting apparatus 15.

The flying organism removing apparatus 400 uses the dielectric cover 522 shown in FIG. 13(a) as the dielectric cover.

The flying organism removing apparatus 400 includes a casing 150, conductors 110a and 110b, dielectrics 520a and 520b, and a power supply 130. As will be described later, the conductor 110a and the dielectric 520a form a dielectric covered conductor 540a, and the conductor 110b and the dielectric 520b form a dielectric covered conductor 540b.

The casing 150 and the power supply 130 have structures and functions similar to the structures and functions of those of the flying organism removing apparatus 100, so that their descriptions will be omitted.

<Conductor 110a, 110b>

As mentioned above, the flying organism removing apparatus 400 includes the conductors 110a and 110b. The conductor 110a comprises nine electric conductors 112a. The conductor 110b comprises nine electric conductors 112b. Those nine electric conductors 112a, 112b are electrically connected to the power supply 130. The nine electric conductors 112a, 112b form "at least one conductor" and "a plurality of electric conductors". The nine electric conductors 112a, 112b are similar to those of the flying organism removing apparatus 200 according to the third embodiment.

<Dielectric 520a, 520b>

As mentioned above, the flying organism removing apparatus 400 includes the dielectrics 520a and 520b. The dielectric 520a comprises nine dielectric covers 522a. The dielectric 520b comprises nine dielectric covers 522b. Those nine dielectric covers 522a, 522b are similar to the dielectric cover 522 shown in FIG. 13(a). The nine dielectric covers 522a and 522b form "at least one dielectric" and "a plurality of dielectric covers".

<Dielectric Covered Conductor 540a, 540b>

The nine electric conductors 112a and the nine dielectric covers 522a form nine dielectric covered conductors 540a, and the nine electric conductors 112b and the nine dielectric covers 522b form nine dielectric covered conductors 540b. The nine dielectric covered conductors 540a and 540b are similar to the dielectric covered conductor 540 shown in FIG. 13(a).

The nine dielectric covered conductors 540a, and the nine dielectric covered conductors 540b, like the nine dielectric covered conductors 140 of the flying organism removing apparatus 100, are disposed to be separated from one another in the perpendicular direction. That is, the nine dielectric covered conductors 140a are disposed in a so-called rattan blind pattern so that a clearance is provided between the adjoining dielectric covered conductors 540a and 540b.

The nine dielectric covered conductors 540a form one "dielectric covered conductor group", and the nine dielectric covered conductors 540b form one "dielectric covered conductor group". Particularly, the nine dielectric covered conductors 540a form the "first dielectric covered conductor group", and the nine dielectric covered conductors 540b form the "second dielectric covered conductor group".

One dielectric covered conductor 540a comprises one electric conductor 112a and one dielectric cover 522a. That is, the flying organism removing apparatus 400 is configured so that one dielectric cover 522a and one electric conductor 112a make a pair. Likewise, one dielectric covered conductor 540b comprises one electric conductor 112b and one dielectric cover 522b. That is, the flying organism removing apparatus 400 is configured so that one dielectric cover 522b and one electric conductor 112b make a pair.

With regard to the vertical (up and down direction to the sheet of FIG. 14) layout of the flying organism removing apparatus 400, it may be disposed in a so-called alternate layout so that one of the nine dielectric covered conductors 540b is disposed between adjoining ones of the nine dielectric covered conductors 540a. When the nine dielectric covered conductors 540b become the reference, the alternative layout is preferable so that one of the nine dielectric covered conductors 540a can be disposed between adjoining ones of the nine dielectric covered conductors 540b.

This layout can allow an electric field to be produced around the nine dielectric covers 522a, 522b by the dielectric polarization caused at the nine dielectric covers 522a, 522b, so that the range of generating the electric field can be made wider. Accordingly, a first electrostatic screen can be formed by the dielectric polarization caused at the nine dielectric covers 522a, and a second electrostatic screen can be formed by the dielectric polarization caused at the nine dielectric covers 522b, and the two electrostatic screens can capture flyable organisms more adequately.

Although the flying organism removing apparatus 400 is illustrated to have two "dielectric covered conductor groups" formed by the nine dielectric covered conductors 540a and 540b, which is not restrictive, three "dielectric covered conductor groups" or more may be formed. This can form three or more electrostatic screens to be able to capture flyable organisms more adequately.

As shown in FIG. 14, the nine dielectric covered conductors 540a are disposed in such a way that the nine dielectric covers 522a face leftward in the diagram, and the nine dielectric covered conductors 540b are disposed in such a way that the nine dielectric covers 522b face rightward in the diagram. That is, outer surfaces 524a of the nine dielectric covers 522a and outer surfaces 524b of the nine dielectric covers 522b are disposed so as to face in the opposite directions. Further, the outer surfaces 524a of the nine dielectric covers 522a are disposed at a position closest to the front surface 168a, and the outer surfaces 524b of the nine dielectric covers 522b are disposed at a position closest to the rear surface 168b. With this layout, even if one touches the nine dielectric covered conductors 540a, 540b when a high voltage is applied to the nine electric conductors 112a, 112b, the nine dielectric covered conductors 540a, 540b are insulated by the nine dielectric covers 522a, 522b, thus securing safety.

Although the flying organism removing apparatus 400 shown in FIG. 14 uses the dielectric covered conductor 540 shown in FIG. 13(a), it may use the dielectric covered conductor 640 shown in FIG. 13(b). In this case, the dielectric covered conductor 640 can be made thinner, so that the thickness of the flying organism removing apparatus 400 (length in the right and left direction in FIG. 14) can be made smaller.

Even if only a part of the electric conductor is covered with a dielectric cover like the dielectric cover 522 shown in FIG. 13(a) or the dielectric cover 622 shown in FIG. 13(b), the dielectric polarization can be caused by the dielectric coverso that an electrostatic field can be generated around the dielectric cover. The electric field generated around the dielectric cover becomes an electric field (non-uniform electric field, uneven field) whose field intensity differs according to the position. When flyable organisms are charged, the Coulomb force can be exerted on the flyable organisms, and when the flyable organisms are electrically neutral, electric induction can be produced at the flyable organism, so that gradient force can be exerted on the flyable organisms. The generation of such an electric field allows the Coulomb force or the gradient force to be exerted on flyable organisms, thus making it difficult for the flyable organisms to move. Accordingly, an electric field generated by the dielectric polarization of the nine dielectric covers 122 forms an electrostatic screen which can adequately capture flyable organisms.

Although the flying organism removing apparatus 400 is illustrated to have each of the nine dielectric covered conductors 540a, 540b disposed horizontally, a plurality of dielectric covered conductors 540a, 540b may be disposed in any way as to permit light to be irradiated on plants placed in the plant arrangement zone 20 and supply air to the plants, and may be disposed perpendicularly or obliquely as well as horizontally. The nine dielectric covered conductors 540a and the nine dielectric covered conductors 540b may be disposed in different directions, so that the nine dielectric covered conductors 540a are disposed horizontally, and the nine dielectric covered conductors 540b are disposed perpendicularly.

FIG. 14 shows a first plane 114a characterizing the general shape of the nine dielectric covered conductors 540a, and a first plane 114b characterizing the general shape of the nine dielectric covered conductors 540b by broken lines. The first planes 114a and 114b can be specified by a scheme similar to that of the flying organism removing apparatus 200.

Other Embodiments

The foregoing flying organism removing apparatus 100, 200, 300 or 400 is illustrated so that a plurality of elongated dielectric covered conductors extending straight are disposed in parallel.

In the flying organism removing apparatus 100 or 300, the nine elongated dielectric covered conductors 140 extending straight are disposed separate from and in parallel to one another. In the flying organism removing apparatus 200, the nine elongated dielectric covered conductors 140a extending straight are disposed separate from and in parallel to one another, and the nine elongated dielectric covered conductors 140b extending straight are disposed separate from and in parallel to one another. Further, in the flying organism removing apparatus 400, the nine elongated dielectric covered conductors 540a extending straight are disposed separate from and in parallel to one another, and the nine elongated dielectric covered conductors 540b extending straight are disposed separate from and in parallel to one another.

The dielectric covered conductor may take a form different from the above forms. For example, a dielectric covered conductor formed into a mesh pattern may be used. As the dielectric covered conductor is formed in a mesh pattern, the flow of air can be disturbed or an air vortex can be generated. The disturbance of the air flow can increases the chance of making flyable organisms present in an area where an electric field produced by the electric conductor, the dielectric or the dielectric covered conductor effectively exists, so that the flyable organisms can be captured or removed adequately.

Further, when the meshed dielectric covered conductor is disposed at a position closest to the front surface 168a of the casing 150, it has the function of a cover for the flying organism removing apparatus, so that movement of objects larger than flyable organisms, such as leaves of plants or dust, can be inhibited by the dielectric mesh body and the objects can be removed so as not to contact the electric conductors.

Furthermore, in case where the meshed dielectric covered conductor is used and only a part of the electric conductor is covered with the dielectric cover as shown in FIG. 13(a) or (b), it is preferable that the outer surface of the dielectric cover should be disposed to face toward the case opening of the casing 150. Specifically, the outer surface of the meshed dielectric cover is disposed to face toward the front surface 168a or rear surface 168b (case opening) of the casing 150. Accordingly, the electric conductor which is not covered with the dielectric cover is not disposed to face toward the case opening, so that even with power supplied to the electric conductor, it can be handled safely.

Further, even if the meshed dielectric covered conductors are used, the meshed dielectric covered conductor may not only be used alone, but may also be combined with the nine dielectric covered conductors used in the flying organism removing apparatus 100, 200, 300 or 400. This can expand the function as an electrostatic screen.

A dielectric formed in a mesh pattern may be used instead of using the meshed dielectric covered conductor. In this case, the meshed dielectric is used together with the flying organism removing apparatus 100, 200, 300 or 400. Specifically, as the meshed dielectric is disposed at a position closest to the front surface 168a of the casing 150, it is allowed to serve as a windshield net for the flying organism removing apparatus 100, 200, 300 or 400, or to serve as a cover to remove leaves of plants or dust. This can prevent wind from entering, or inhibit movement of objects larger than flyable organisms, such as leaves of plants or dust, by using the meshed dielectric. Further, a shutter or glass may be provided at a position closest to the front surface 168a of the casing 150. When a meshed dielectric, or a shutter or glass is provided, it is preferable light enters to the extent not affecting the growing of plants. For example, the transmittance of light at this time is preferably 50% or greater, or is more preferably 60% or greater.

Further, particularly, when it rains or there is a gale, it is preferable to put a cover or the like over the flying organism removing apparatus 100, 200, 300 or 400. Available covers include one which covers with a vinyl sheet, a shutter, or a glass door.

EXAMPLES

In the next place, the present invention will be described more specifically by way of example and comparative example, which are not restrictive.

Example 1

A copper wire covered with a non-conductor (vinyl covered copper wire having a thickness of about 1.2 mm) was charged (to about 15 kV) using a van de Graff type electrostatic generator and checked if conidia of tomato powdery mildew would be trapped. That is, leaves of tomato infected by powdery mildew were placed 50 cm from the non-conductor covered copper wire, and it was observed with a microscope (for 30 seconds, magnification of ×250) whether the conidia were trapped on the non-conductor covered copper wire before and after charging. The results showed that conidia were not trapped on the non-conductor covered copper before charging, while conidia were trapped on the non-conductor covered copper after charging.

It was checked if the trapped conidia would germinate or propagate. The results showed that the conidia germinated but did not propagate.

Example 2

Figure 3:
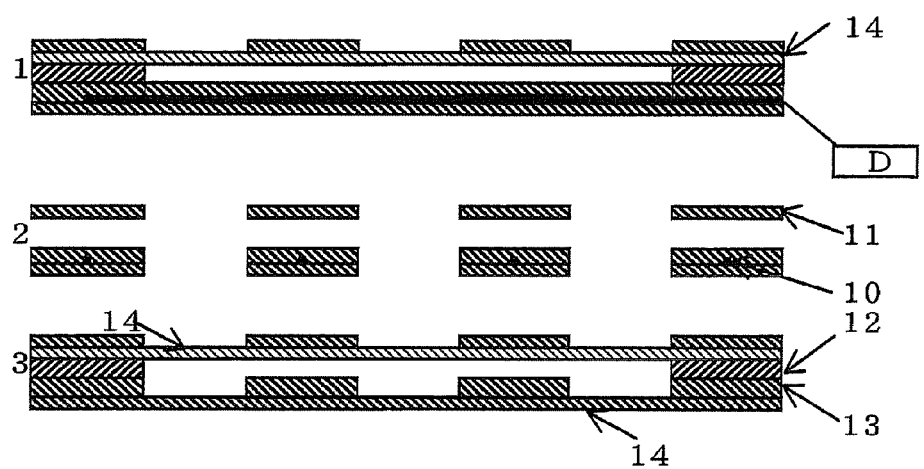
Figure 4:
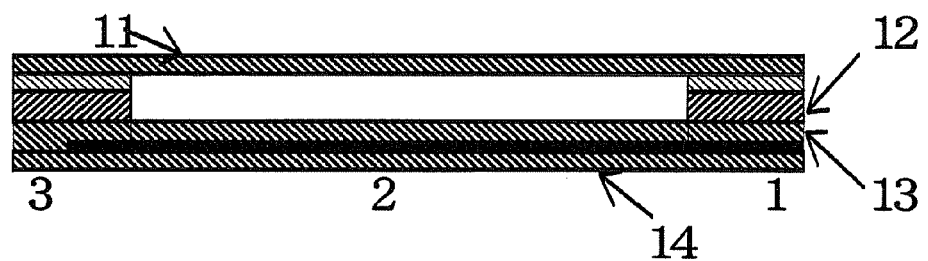

The apparatus as shown in FIG. 1 was prepared (FIG. 1 is a conceptual diagram) and the behavior of conidia was checked. That is, an aluminum plate of 0.25×8 cm is adhered to a polyethylene terephthalate (PET) plate with a thickness of 0.5 mm and 0.5×10 cm, and fixed with an insulative tape (electrode portion covered with a non-conductor), and it was connected to a high voltage generator (prepared by referring to a high voltage output circuit for a photomultiplier) using a vinyl chloride covered copper wire. Six sets of electrode portions (electrode portions 13 in FIG. 3 or FIG. 4) were set in parallel at equal intervals using two PET plates of 0.5 mm×1×10 cm (14 in FIG. 3 or FIG. 4). Further, six sets of PET plates of 0.5 mm×1×10 cm were set in parallel at equal intervals using two PET plates of 0.5 mm×1×10 cm (non-moving portion 11 in FIG. 3 or FIG. 4). Those electrode portions 13 and non-moving portions 11 are arranged in parallel using four spacers (12 in FIG. 3 or FIG. 4) (in such a way that the non-moving portion were set over the dielectric polarization applying section and the electrode portions 13.) The thickness of the spacers were set to 7 mm or 9 mm.

The dielectric polarization applying section was set at the A portion in FIG. 1, and the electrode portion were charged with −15 kV or −5 kV (the other one to the polarity connected to the electrode portion being grounded). Then, conidia of tomato powdery mildew were dropped from above (C), and their adhesion to the dielectric polarization applying section was checked.

As a result, in the case where a high voltage is not applied to the dielectric polarization applying section, the conidia passed through and were observed at a B portion, but when it was charged, the conidia adsorbed to the dielectric polarization applying section and conidia at the B portion were not observed at any voltage.

Example 3

Copper wires covered with a non-conductor (vinyl covered copper wire having a thickness of about 1.2 mm) were set up to a polyethylene frame in a vertical and horizontal grid pattern at intervals of about 5 mm, and were connected, at one ends, to a high voltage generator (dielectric polarization applying section). This dielectric polarization applying section was set at the A portion in FIG. 1, and charged to −15 kV or −5 kV (the other one to the polarity connected to the electrode portion being grounded). Then, conidia of tomato powdery mildew were dropped from above (C), and their adhesion to the dielectric polarization applying section was checked.

As a result, in the case where a high voltage is not applied to the dielectric polarization applying section, the conidia passed through and were observed at a B portion, but when it was charged, the conidia adsorbed to the dielectric polarization applying section and conidia at the B portion were not observed.

Example 4

Similar manipulation to that of Example 2 was performed except that tomato seedling was placed instead of a slide glass at the B portion. Then the tomato seedling was grown for eight days.

As a result, in the case where a high voltage is not applied to the dielectric polarization applying section, germinating of powdery mildew on the tomato seedling was observed, whereas when it was charged, germinating of powdery mildew was not observed. This result did not change even if the charge voltage or the interval between the spacers was changed.

Example 5

Similar manipulation to that of Example 3 was performed except that tomato seedling was placed instead of a slide glass at the B portion. Then the tomato seedling was grown for eight days.

As a result, in the case where a high voltage is not applied to the dielectric polarization applying section, germinating of powdery mildew on the tomato seedling was observed, whereas when it was charged, germinating of powdery mildew was not observed. This result did not change even if the charge voltage or the interval between the spacers was changed.

Example 6

The foregoing plant protecting apparatus 15 was placed in a greenhouse, and the effects of removing tomato powdery mildew and small vermin (Agromyzidae, silverleaf whitefly, rust mites) were checked.

The plant protecting apparatus has a box-like shape of 80 cm horizontal, 50 cm in height and 50 cm in depth and covered with an acrylic resin plate. The flying organism removing apparatus 100 according to the second embodiment was set at five sides of the plant protecting apparatus 15 (two side faces, top face, front face, rear face) to serve as an electrostatic screen. The flying organism removing apparatus 100 including the nine dielectric covered conductors 140 was used. The nine dielectric covered conductors 140 were arranged in a rattan blind pattern so that the interval between the adjoining dielectric covered conductors 140 became 3 cm. The dielectric covered conductor 140 has an acrylic cylinder (diameter of 1 cm) as the dielectric cover 122, and a copper wire, as the electric conductor 112, placed inside the acrylic cylinder (approximately along the axial center line). Each copper wire was connected to the negative polarity of the DC low-current/high-voltage generator, and the positive polarity thereof was grounded to apply 20 kV to each copper wire.

Healthy tomato seedling (type: Micro-Tom) was placed inside the plant protecting apparatus 15, tomato seedling infected by powdery mildew and tomato seedling on which small vermin (Agromyzidae, silverleaf whitefly, rust mites) bred were placed in a greenhouse.

The seedlings were grown until blooming of flowers and seed setting from the seedling stage after voltage application (about three months). As a result, infection of powdery mildew and generation of small vermin (Agromyzidae, silverleaf whitefly, rust mites) were observed on the tomato seedling outside the plant protecting apparatus, while neither event was observed on tomato inside the plant protecting apparatus.

Example 7

The flying organism removing apparatus according to the second embodiment was used in this Example 7. Specifically, a box of 50 cm horizontal, 30 cm in height and 25 cm in depth was prepared by an acrylic resin plate, and twelve dielectric covered conductors 140 were provided in the center portion of the box to provide an electrostatic screen function. The twelve dielectric covered conductors 140 were arranged in a rattan blind pattern so that the interval between the adjoining dielectric covered conductors 140 became 1 cm. The dielectric covered conductor 140 is a vinyl chloride covered copper wire (diameter of 1.2 mm). Each vinyl chloride covered copper wire was connected to the negative polarity of the DC low-current/high-voltage generator, and the positive polarity thereof was grounded to apply 20 kV to each vinyl chloride covered copper wire.

In the experiment, 86 Mycetophilidae (generated in mushroom bed) were released on the left-hand side of the laboratory equipment, and healthy mushroom bed was placed on the right-hand side thereof.

The observation of the Mycetophilidae released after two hours showed that there were no Mycetophilidae moved through the electrostatic screen to the right side where the health mushroom bed was present. In the two-hour observation, there were 21 Mycetophilidae captured by the electrostatic screen, 32 Mycetophilidae which approached the electrostatic screen and fled, and 33 Mycetophilidae which did not attempt to enter.

The experiment in which no voltage was applied was similarly conducted as a comparative example (86 Mycetophilidae released), showing that 50 Mycetophilidae moved through the cylinder into the right-hand side of the equipment where healthy mushroom bed was placed.

INDUSTRIAL APPLICABILITY

The method of removing conidia and microbe or the like by dielectric polarization can efficiently remove conidia and microbe or the like, which cause a plant disease, from air, and does not generate ozone originated from discharge or the like, and can thus be used to prevent occurrence of a plant disease without damaging plants.

The invention claimed is:
1. A flying organism removing apparatus comprising:
 a plurality of electric conductors,
 a power supply which is electrically connected to the plurality of electric conductors and sets the plurality of electric conductors to a predetermined potential in such a way that an electric field is generated by the plurality of electric conductors; and
 a plurality of dielectric covers located at a position where dielectric polarization is caused by the electric field generated by the plurality of electric conductors,
 wherein a plurality of dielectric covered conductors are formed by the plurality of electric conductors and the plurality of dielectric covers,
 each of the plurality of dielectric covered conductors is formed by a pair of one of the plurality of electric conductors and one of the plurality of dielectric covers,
 a plurality of dielectric covered conductor groups are formed by the plurality of dielectric covered conductors,
 each of the plurality of dielectric covered conductor groups is formed by a predetermined number of dielectric covered conductors in the plurality of dielectric covered conductors,
 each of the plurality of dielectric covered conductor groups is arranged along one corresponding surface in a plurality of predetermined surfaces different from one another, and
 a flying organism can be captured by an electric field generated via the plurality of dielectric covers.

2. The flying organism removing apparatus according to claim 1, wherein the plurality of dielectric covered conductor groups include a first dielectric covered conductor group and a second dielectric covered conductor group,
 wherein the first dielectric covered conductor group and the second dielectric covered conductor group are positioned at an outermost surface of the plurality of predetermined surfaces different from one another, and the electric conductor is covered with the dielectric cover at least at the outer side of the outermost surfaces in each of the dielectric covered conductors forming the first dielectric covered conductor group and the second dielectric covered conductor group.

3. The flying organism removing apparatus according to claim 1, wherein at least one dielectric covered conductor forming one dielectric covered conductor group is positioned between adjoining ones of the dielectric covered conductors forming the dielectric covered conductor group adjoining the one dielectric covered conductor group.

4. The flying organism removing apparatus according to claim 1, wherein the plurality of electric conductors is charged to a positive voltage or a negative voltage by the power supply.

5. The flying organism removing apparatus according to claim 1, wherein the plurality of dielectric covered conductors forming each of the plurality of dielectric covered conductor groups are supported by flexible elongated supports.

6. The flying organism removing apparatus according to claim 1, wherein at least a part of the electric conductor is covered with the dielectric cover forming the same dielectric covered conductor.

7. The flying organism removing apparatus according to claim 6, wherein each of the plurality of electric conductors has an approximately rod shape,
each of the plurality of dielectric covers has an approximately cylindrical shape,
the electric conductor is arranged inside the dielectric cover along a longitudinal direction thereof, and
the plurality of dielectric covered conductors are arranged to be separated from and in parallel to one another to permit air to flow.

8. The flying organism removing apparatus according to claim 6, wherein each of the plurality of electric conductors has an approximately rod shape,
each of the plurality of dielectric covers has an approximately semicylindrical shape including an outer surface and an inner surface,
the electric conductor is arranged on an inner surface side of the dielectric cover and along a longitudinal direction thereof, and
the plurality of dielectric covered conductors are arranged to be separated from and in parallel to one another to permit air to flow.

9. The flying organism removing apparatus according to claim 1, wherein at least one dielectric covered conductor group of the plurality of dielectric covered conductor groups is arranged so as to cover a predetermined opening formed to permit air to flow.

10. A plant protecting apparatus comprising:
a plant arrangement zone where a plant is arranged; and
a surrounding part surrounding the plant arrangement zone,
wherein at least a part of the surrounding part can transmit visible light, and
the flying organism removing apparatus as set forth in claim 1 is provided in the portion of the surrounding part where air can flow.

11. A method of preventing occurrence of a plant disease by using the flying organism removing apparatus as set forth in claim 1, wherein the flying organism is charged with a high electrostatic voltage by the dielectric covers contacting the electric conductors charged with a high voltage or the dielectric covers adjacent thereto, and the charged flying organism is adsorbed by the dielectric covers to be removed from the air.

12. A method of preventing occurrence of a plant disease by using the flying organism removing apparatus as set forth in claim 1, wherein the flying organism can be captured by an electrostatic screen formed by an electric field generated by the dielectric polarization of the dielectric covers.

* * * * *